(12) United States Patent
Doschak et al.

(10) Patent No.: US 8,772,235 B2
(45) Date of Patent: Jul. 8, 2014

(54) COMPOUNDS HAVING PEPTIDES CONJUGATED TO BONE TARGETING MOIETIES AND METHODS OF MAKING AND USING THEREOF

(75) Inventors: Michael R. Doschak, Edmonton (CA); Krishna Hari Bhandari, Edmonton (CA)

(73) Assignee: The Governors of the University of Alberta, Edmonton (CA)

(*) Notice: Subject to any disclaimer, the term of this patent is extended or adjusted under 35 U.S.C. 154(b) by 0 days.

(21) Appl. No.: 13/501,652

(22) PCT Filed: Oct. 12, 2010

(86) PCT No.: PCT/IB2010/002708
§ 371 (c)(1),
(2), (4) Date: Jul. 2, 2012

(87) PCT Pub. No.: WO2011/045668
PCT Pub. Date: Apr. 21, 2011

(65) Prior Publication Data
US 2012/0270787 A1    Oct. 25, 2012

Related U.S. Application Data

(60) Provisional application No. 61/251,472, filed on Oct. 14, 2009.

(51) Int. Cl.
*A61K 47/48* (2006.01)
*A61K 38/23* (2006.01)
*A61P 19/08* (2006.01)

(52) U.S. Cl.
CPC .................................... *A61K 47/48* (2013.01)
USPC ........................................ 514/11.9; 530/399

(58) Field of Classification Search
None
See application file for complete search history.

(56) References Cited

FOREIGN PATENT DOCUMENTS

| CA | 2279590 | 2/1998 |
| EP | 0512844 | 11/1992 |
| WO | 02083150 | 10/2002 |

OTHER PUBLICATIONS

Gittens et al. "Designing proteins for bone targeting" (2005) Advanced Drug Delivery Reviews 57: 1011-1036.*
Uludag et al. "Bone Affinity of a Biosphosphonate-Conjugated Protein in Vivo" (2000) Biotechnol. Prog. 16(6): 1115-1118.*
Zaidi et al. "Biology of peptides from the calcitonin genes" (Oct. 1987) Quarterly Journal of Experimental Physiology 72: 371-408.*
Bansal et al. "A Di(Bisphoshonic acid) for Protein Coupling and Targeting to Bone", Journal of Pharmaceutical Sciences. vol. 93, No. 11. Nov. 2004.
Bhandari et al. "Synthesis, characterization and in vitro evaluation of a bone targeting delivery system for salmon Calcitonin" International Journal of Pharmaceutics 394 (2010) 26-34.
Cetin et al "Preparation and Characterization of Salmon Calcitonin-biotin Conjugates" AAPS PharmSciTech, vol. 9, No. 4, Dec. 2008.
Gittens et al. "Designing proteins for bone targeting" Advanced Drug Delivery Reviews 57 (2005) 1011-1036.
International Search Report for international application No. PCT/IB2010/002708.
Cheng et al. "Aqueous-Soluble, Non-Reversible Lipid Conjugate of Salmon Calcitonin: Synthesis, Characterization and In Vivo Activity" Pharm Research vol. 24, No. 1, Jan. 2007.
Ogaga et al "Effects of combined elcatonin and alendronate treatment on the architecture and strength of bone in ovariectomized rats" J Bone Miner Metab (2005) 23:351-358.
Sekine et al. "Combination of calcitonin and pamidronate for emergency treatment of malignant hypercalcemia" Oncology Reports 5: 197-199. 1998.
Smoum et al "Chitosan-Pentaglycine-Phenylboronic Acid Conjugate: A Potential Colon-Specific Platform for Calcitonin" Bioconjugate Chem. 2006, 17, 1000-1007.
Wang et al. Bone-targeting macromolecular therapeutics, Advanced Drug Delivery Reviews 57 (2005) 1049-1076.
Zhang et al. Magic bullets' for bone diseases: progress in rational design of bone-seeking medicinal agents, Chern. Soc. Rev., 2007, 36, 507-531.
Uludag Bisphosphonates as a foundation of drug delivery to bone, Current Pharmaceutical Design, 2002, 8, 1929-1944.

* cited by examiner

*Primary Examiner* — Jean Witz
*Assistant Examiner* — Mindy Newman
(74) *Attorney, Agent, or Firm* — Gardner, Groff, Greenwald, & Villanueva P.C.

(57) ABSTRACT

Described herein are compositions having a peptide sequence that includes at least one bone targeting moiety, wherein the bone targeting moiety is bonded to the peptide sequence by a linker, wherein the peptide sequence is calcitonin, and wherein the composition is neutral or a pharmaceutically acceptable salt or ester thereof. In one aspect, calcitonin inhibits or slows osteoclast mediated resorptive bone loss. The compounds described herein can be used in a number of therapeutic applications including treating or preventing conditions associated with bone loss, which include, but are not limited to, osteoporosis, Paget's disease, osteolytic tumors, Rheumatoid Arthritis, Psoriatic Arthritis, Ankylosing Spondylitis, Osteoarthritis, osteopenia, and hypercalcemia. Also described herein are the methods of making these compositions that prevent or treat conditions associated with bone loss and methods of preventing bone fractures.

29 Claims, 22 Drawing Sheets

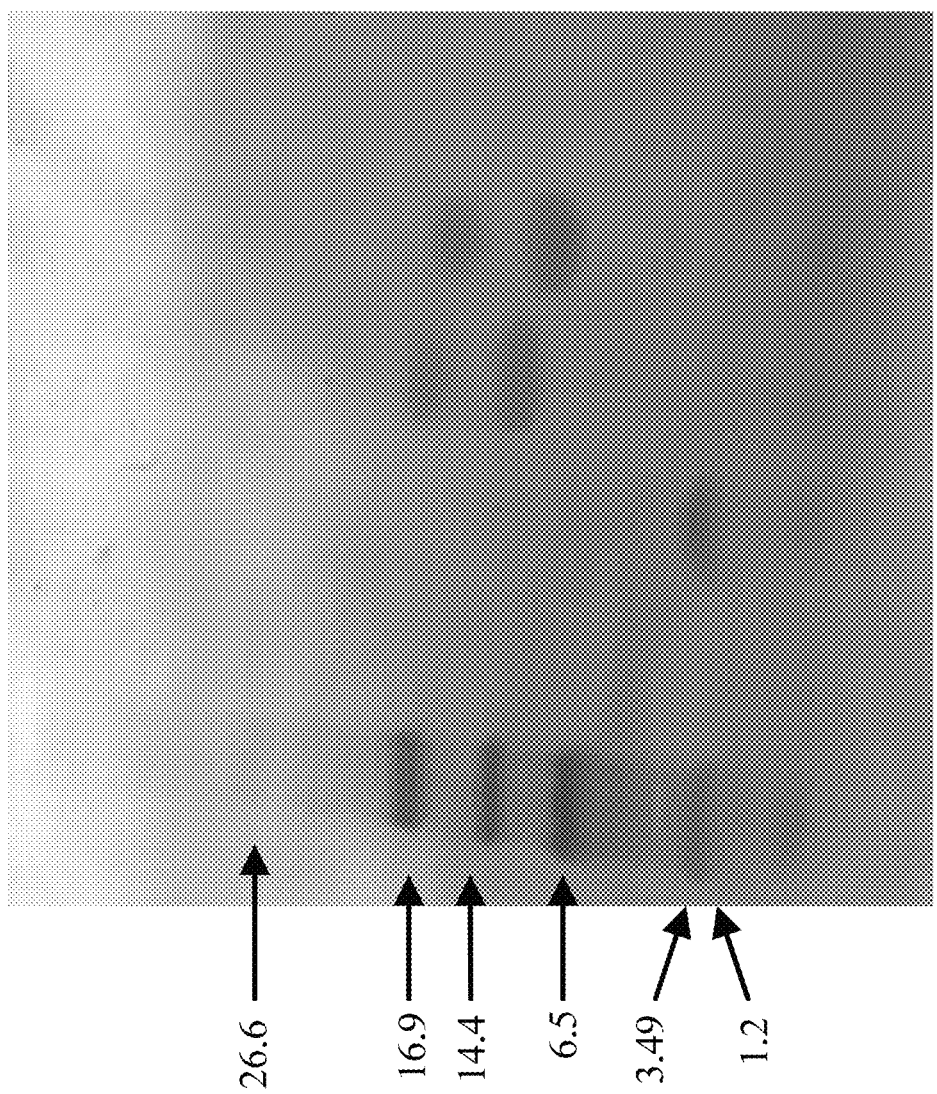

SEQUENCE LISTING

<160> NUMBER OF SEQ ID NOS: 15

<210> SEQ ID NO 1
<211> LENGTH: 32
<212> TYPE: PRT
<213> ORGANISM: Oncorhynchus gorbuscha

<400> SEQUENCE: 1

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30

<210> SEQ ID NO 2
<211> LENGTH: 32
<212> TYPE: PRT
<213> ORGANISM: Homo sapiens

<400> SEQUENCE: 2

Cys Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30

<210> SEQ ID NO 3
<211> LENGTH: 32
<212> TYPE: PRT
<213> ORGANISM: Anguilla anguilla

<400> SEQUENCE: 3

Cys Ser Asn Leu Ser Thr Cys Val Leu Gly Lys Leu Ser Gln Glu Leu
1               5                   10                  15

His Lys Leu Gln Thr Tyr Pro Arg Thr Asp Val Gly Ala Gly Thr Pro
            20                  25                  30

<210> SEQ ID NO 4
<211> LENGTH: 31
<212> TYPE: PRT
<213> ORGANISM: Dasyatis akajei

<400> SEQUENCE: 4

Cys Thr Ser Leu Ser Thr Cys Val Val Gly Lys Ser Gln Gln Leu His
1               5                   10                  15

Lys Leu Gln Asn Ile Gln Arg Thr Asp Val Gly Ala Ala Thr Pro
            20                  25                  30

<210> SEQ ID NO 5
<211> LENGTH: 32
<212> TYPE: PRT
<213> ORGANISM: Sus scrofa

<400> SEQUENCE: 5

Cys Ser Asn Leu Ser Thr Cys Val Leu Ser Ala Tyr Trp Arg Asn Leu
1               5                   10                  15

Asn Asn Phe His Arg Phe Ser Gly Met Gly Phe Gly Pro Glu Thr Pro
            20                  25                  30

<210> SEQ ID NO 6
<211> LENGTH: 32
<212> TYPE: PRT
<213> ORGANISM: Gallus gallus

<400> SEQUENCE: 6

```
Cys Ala Ser Leu Ser Thr Cys Val Leu Gly Lys Leu Ser Gln Glu Leu
1               5                   10                  15

His Lys Leu Gln Thr Tyr Pro Arg Thr Asp Val Gly Ala Gly Thr Pro
            20                  25                  30
```

<210> SEQ ID NO 7
<211> LENGTH: 32
<212> TYPE: PRT
<213> ORGANISM: Sardinops melanostictus

<400> SEQUENCE: 7

```
Cys Ser Asn Leu Ser Thr Cys Ala Leu Gly Lys Leu Ser Gln Glu Leu
1               5                   10                  15

His Lys Leu Gln Ser Tyr Pro Arg Thr Asn Val Gly Ala Gly Thr Pro
            20                  25                  30
```

<210> SEQ ID NO 8
<211> LENGTH: 56
<212> TYPE: PRT
<213> ORGANISM: Oncorhynchus gorbuscha

<400> SEQUENCE: 8

```
Lys Arg Cys Ser Asn Leu Ser Thr Cys Val Leu Gly Lys Leu Ser Gln
1               5                   10                  15

Glu Leu His Lys Leu Gln Thr Tyr Pro Arg Thr Asn Thr Gly Ser Gly
            20                  25                  30

Thr Pro Gly Lys Lys Arg Ser Leu Pro Glu Ser Asn Arg Tyr Ala Ser
        35                  40                  45

Tyr Gly Asp Ser Tyr Asp Gly Ile
        50                  55
```

<210> SEQ ID NO 9
<211> LENGTH: 50
<212> TYPE: PRT
<213> ORGANISM: Paralichthys olivaceus

<400> SEQUENCE: 9

```
Cys Thr Gly Leu Ser Thr Cys Val Leu Gly Lys Leu Ser Gln Asp Ile
1               5                   10                  15

His Lys Leu Gln Thr Tyr Pro Arg Thr Asn Val Gly Ala Gly Thr Pro
            20                  25                  30

Gly Lys Lys Arg Ser Leu Ser Glu Gln Tyr Glu Asn His Gly Ser Ser
        35                  40                  45

Tyr Asn
    50
```

<210> SEQ ID NO 10
<211> LENGTH: 32
<212> TYPE: PRT
<213> ORGANISM: Canis familiaris

<400> SEQUENCE: 10

```
Cys Ser Asn Leu Ser Thr Cys Val Leu Gly Thr Tyr Ser Lys Asp Leu
1               5                   10                  15

Asn Asn Phe His Thr Phe Ser Gly Ile Gly Phe Gly Ala Glu Thr Pro
            20                  25                  30
```

<210> SEQ ID NO 11
<211> LENGTH: 33
<212> TYPE: PRT

```
<213> ORGANISM: Artificial Sequence
<220> FEATURE:
<223> OTHER INFORMATION: synthetic construct

<400> SEQUENCE: 11

Met Cys Gly Asn Leu Ser Thr Cys Met Leu Gly Thr Tyr Thr Gln Asp
1               5                   10                  15

Phe Asn Lys Phe His Thr Phe Pro Gln Thr Ala Ile Gly Val Gly Ala
            20                  25                  30

Pro

<210> SEQ ID NO 12
<211> LENGTH: 48
<212> TYPE: PRT
<213> ORGANISM: Mus musculus

<400> SEQUENCE: 12

Ser Leu Asp Ser Pro Arg Ser Lys Arg Cys Gly Asn Leu Ser Thr Cys
1               5                   10                  15

Met Leu Gly Thr Tyr Thr Gln Asp Leu Asn Glu Phe His Thr Phe Pro
            20                  25                  30

Gln Thr Ser Ile Gly Val Glu Ala Pro Gly Lys Lys Arg Asp Val Ala
            35                  40                  45

<210> SEQ ID NO 13
<211> LENGTH: 32
<212> TYPE: PRT
<213> ORGANISM: Carassius auratus

<400> SEQUENCE: 13

Cys Ser Ser Leu Ser Thr Cys Val Leu Gly Lys Leu Ser Gln Glu Leu
1               5                   10                  15

His Lys Leu Gln Thr Tyr Pro Arg Thr Asn Val Gly Ala Gly Thr Pro
            20                  25                  30

<210> SEQ ID NO 14
<211> LENGTH: 32
<212> TYPE: PRT
<213> ORGANISM: Salvelinus alpinus

<400> SEQUENCE: 14

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30

<210> SEQ ID NO 15
<211> LENGTH: 32
<212> TYPE: PRT
<213> ORGANISM: Salmo salar

<400> SEQUENCE: 15

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30
```

COMPOUNDS HAVING PEPTIDES CONJUGATED TO BONE TARGETING MOIETIES AND METHODS OF MAKING AND USING THEREOF

CROSS REFERENCE TO RELATED APPLICATION

This application claims priority upon U.S. provisional application Ser. No. 61/251,472, filed Oct. 14, 2009. This application is hereby incorporated by reference in its entirety for all of its teachings.

BACKGROUND

Conditions that cause loss of bone mass and micro-architectural deterioration of bone structure affect many worldwide. For example, 44 million people age 50 or older are affected by osteoporosis in the United States alone. In addition, other conditions including, but not limited to, Paget's disease, osteolytic tumors, Rheumatoid Arthritis, Psoriatic Arthritis, Ankylosing Spondylitis, Osteoarthritis, osteopenia including drug induced osteopenia, and hypercalcemia also cause loss of bone mass and affect hundreds of millions of people worldwide.

These conditions predispose those suffering from these maladies to enhanced bone fragility and risk of fracture. Each condition has various etiologies such as congenital conditions, malnutrition, or various additional factors. For example, osteoporosis alone has at least three etiologies. The etiologies for osteoporosis have been established based on predisposing factors and clinical presentation, namely: postmenopausal (type I), senile (type II), and secondary (type III) osteoporosis. In all types, the declining ability of the bone remodeling machinery results in bone fragility. Type I postmenopausal osteoporosis (PMOP) occurs in women 51-75 years of age, in which, estrogen deficiency shifts bone remodeling to favor bone resorption over bone formation, which results in a net bone loss. Type II senile osteoporosis affects women at about twice the rate as men, and occurs from ages 75 to 90 years. Type III or secondary osteoporosis is caused by medications, cancers, endocrine disorders, chronic liver or kidney diseases, and additional conditions. The net result for each type of osteoporosis is the insidious loss of bone mass and the predisposition to traumatic bone fracture.

Numerous treatments have been administered to patients with these conditions; these treatments include the administration of hormone replacement therapy, antiresorptive agents, and immunosuppressants including monoclonal antibodies. However, administering therapeutic levels of these treatments often result in various side effects. For example, some treatments have been linked to various cancers, bone necrosis or osteonecrosis, and other unwanted side effects. Therefore, it is generally difficult to efficiently treat or prevent conditions that cause bone loss with the currently known compositions and methods.

SUMMARY

Described herein are compositions having a peptide sequence that includes at least one bone targeting moiety, wherein the bone targeting moiety is bonded to the peptide sequence by a linker, wherein the peptide sequence is calcitonin, and wherein the composition is neutral or a pharmaceutically acceptable salt or ester thereof. In one aspect, calcitonin inhibits or slows osteoclast mediated resorptive bone loss. The compounds described herein can be used in a number of therapeutic applications including treating or preventing conditions associated with bone loss, which include, but are not limited to, osteoporosis, Paget's disease, osteolytic tumors, Rheumatoid Arthritis, Psoriatic Arthritis, Ankylosing Spondylitis, Osteoarthritis, osteopenia, and hypercalcemia. Also described herein are the methods of making these compositions that prevent or treat conditions associated with bone loss and methods of preventing bone fractures. The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

FIG. 9 shows the tris-tricine-SDS-PAGE of reaction mixtures. (Left to right) Lane 1. Peptide SDS-PAGE Molecular Weight Standards. 2. Salmon calcitonin 3. sCT-PEG-BP Conjugate. 4. sCT-PEG-MAL intermediate.

DETAILED DESCRIPTION

Figure 1:
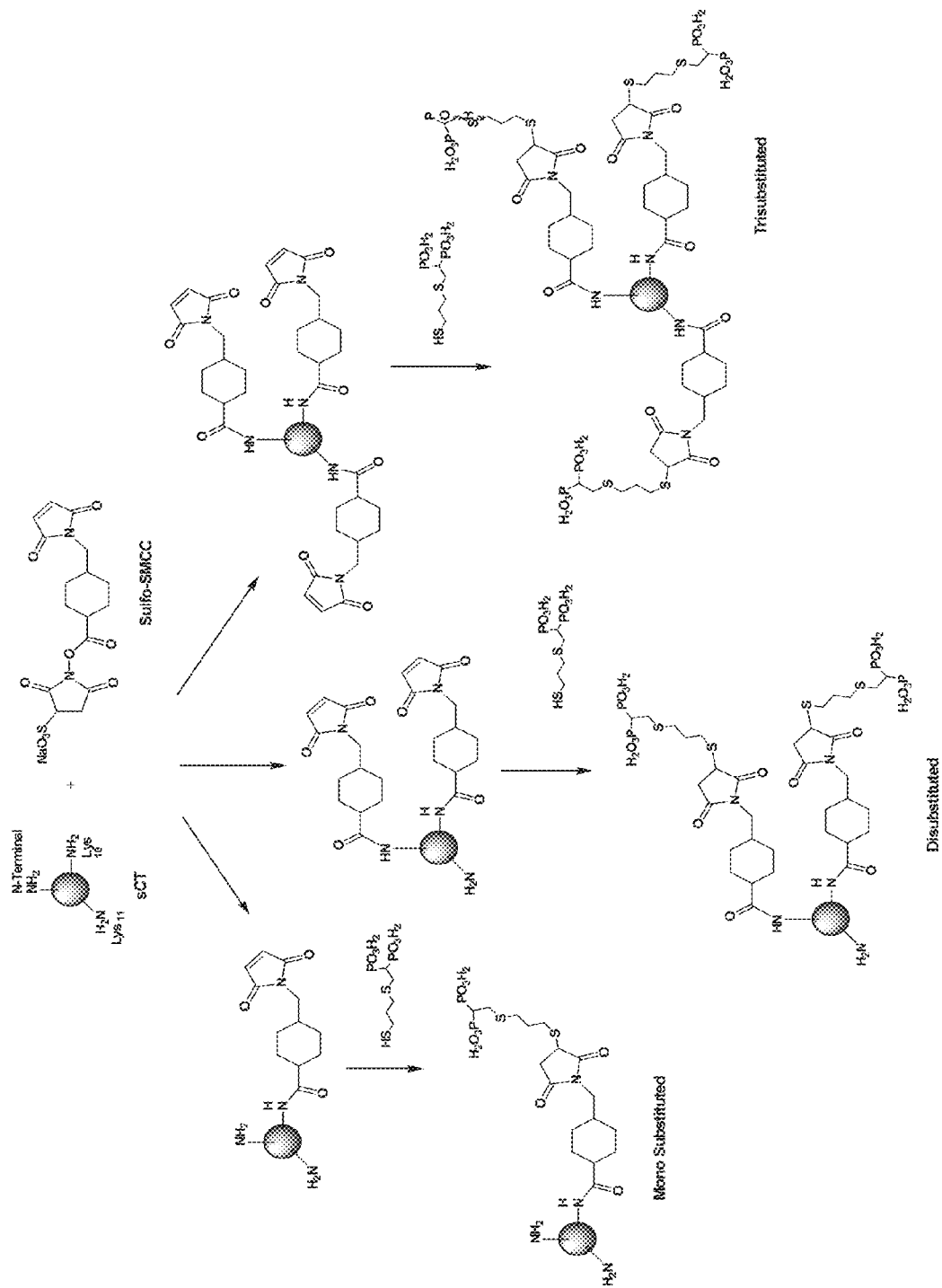
FIG. 1 shows the probable products when sCT is reacted with sulfo-SMCC followed by the reaction of sCT-SMCC intermediate with Thiol-BP.

Before the present compounds, compositions, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not. For example, the phrase "optionally PEGylated" means that a polyethylene glycol group can or cannot be present in the compositions described herein.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

"Subject" refers to mammals including, but not limited to, humans, non-human primates, sheep, dogs, rodents (e.g., mouse, rat, etc.), guinea pigs, cats, rabbits, cows, and non-mammals including chickens, amphibians, and reptiles, who are at risk for or have been diagnosed with a condition that causes bone loss and benefits from the methods and compositions described herein.

"Vertebrate" refers to any animal within the phylum Chordata and subphylum Vertebrata. For example, vertebrate can refer to fish, amphibians, reptiles, birds, and mammals. More particularly, vertebrate as used herein can include, but is not limited to, salmon, human, pig, eel, ray fish, bovine, chicken, rat, mouse, bastard halibut or olive flounder, dog, sardine, goldfish, arctic charr, atlantic salmon, and humpback salmon.

"Peptide" or "peptide sequence" may be used to refer to a natural or synthetic molecule comprising two or more amino acids linked by the carboxyl group of one amino acid to the alpha amino group of another. The peptide is not limited by length, and thus "peptide" can include a peptide fragment, a polypeptide(s), and full-length proteins.

When describing variants in proteins or peptides, the term "variant" refers to an amino acid or peptide sequence having conservative amino acid substitutions, non-conservative amino acid substitutions (i.e. a degenerate variant), substitutions within the wobble position of each codon (i.e. DNA and RNA) encoding an amino acid, amino acids added to the C-terminus of a peptide, or a peptide having 60%, 65%, 70%, 75%, 80%, 85%, 90%, 95%, 96%, 97%, 98%, or 99% homology to a reference sequence.

The terms "homology," "identity or identical," and "similarity" refer to the degree of sequence similarity between two peptides or between two optimally aligned nucleic acid molecules. Homology and identity can each be determined by comparing a position in each sequence which can be aligned for purposes of comparison. For example, it is based upon using a standard homology software in the default position, such as BLAST, version 2.2.14. When an equivalent position in the compared sequences is occupied by the same base or amino acid, then the molecules are identical at that position; when the equivalent site occupied by similar amino acid residues (e.g., similar in steric and/or electronic nature such as, for example conservative amino acid substitutions), then the molecules can be referred to as homologous (similar) at that position. Expression as a percentage of homology/similarity or identity refers to a function of the number of similar or identical amino acids at positions shared by the compared sequences, respectfully. A sequence which is "unrelated" or "non-homologous" shares less than 40% identity, though preferably less than 25% identity with the sequences as disclosed herein.

As used herein, the term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T. C, G. U. or I) or residue occurs in both sequences to yield the number of matched positions, dividing the number of matched positions by the total number of positions in the comparison window (i.e., the window size), and multiplying the result by 100 to yield the percentage of sequence identity.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. For example, a targeting moiety that contains at least one —SH group can be represented by the formula Y—SH, where Y is the remainder (i.e., residue) of the targeting moiety.

The term "linker" refers to a chemical group that is capable of covalently linking the peptides described herein to a bone targeting moiety such as the bone targeting moieties described herein. Structural information regarding the linkers used herein is provided below.

"Bone targeting moiety" refers to any chemical compound, peptide, or nucleic acid that has an affinity for bone mineral, matrix and/or cells, including bone hydroxyapatite, osteocytes, osteoblasts, osteoclasts or any combination thereof and is capable of selectively targeting bone mineral, matrix and/or cells including hydroxyapatite, osteocytes, osteoblasts, osteoclasts, or any combination thereof over other cells and tissues. Structural information regarding the bone targeting moieties used herein is provided below.

The term "alkyl group" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is an alkyl group containing from one to six carbon atoms.

The term "alkylene group" as used herein is a branched or unbranched unsaturated hydrocarbon group of 1 to 24 carbon atoms such as methylene, ethylene, propene, butylene, isobutylene and the like.

The term "cycloalkyl group" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulphur, or phosphorus.

The term "aryl group" as used herein is any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, halo, hydroxy, alkylthio, arylthio, alkoxy, aryloxy, amino, mono- or di-substituted amino, ammonio or substituted ammonio, nitroso, cyano, sulfonato, mercapto, nitro, oxo, alkyl, alkenyl, cycloalkyl, benzyl, phenyl, substituted benzyl, substituted phenyl, benzylcarbonyl, phenylcarbonyl, saccharides, substituted benzylcarbonyl, substituted phenylcarbonyl and phosphorus derivatives. The aryl group can include two or more fused rings, where at least one of the rings is an aromatic ring. Examples include naphthalene, anthracene, and other fused aromatic compounds.

The term "alkyl thiol" as used herein can refer to the general formula —RSH wherein R includes an alkyl group as defined above.

The term "alkylene thiol" as used herein can refer to the general formula —RSH wherein R includes an alkylene group as defined above.

The term "aryl thiol" as used herein can refer to the general formula —RSH wherein R includes an aryl group as defined above.

The term "alkyl thioether" as used herein can refer to the general formula —R—S—R$^1$ wherein R and R$^1$ can independently include alkyl groups as defined above.

The term "alkylene thioether" as used herein can refer to the general formula —R—S—R$^1$ wherein R and R$^1$ can independently include alkylene groups as defined above.

The term "amino alkyl thiol group" as used herein can refer to the general formula —N(R$^3$)—R—SH, wherein R$^3$ is hydrogen or an alkyl group and R is an alkyl group as defined herein.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within the ranges as if each numerical value and sub-range is explicitly recited. As an illustration, a numerical range of "about 1 to 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc. as well as 1, 2, 3, 4, and 5, individually. The same principle applies to ranges reciting only one numerical value as a minimum or a maximum. Furthermore, such an interpretation should apply regardless of the breadth of the range or the characteristics being described.

1. Compositions:

Described herein are compositions having a peptide sequence that include at least one bone targeting moiety, wherein the targeting moiety is bonded to the peptide sequence by a linker and wherein the composition is neutral or a pharmaceutically acceptable salt or ester thereof.

In some aspects, the peptide sequence is an anti-resorptive agent that slows or inhibits osteoclast mediated resorptive bone loss. In this aspect, the peptide can include a vertebrate calcitonin; wherein the calcitonin can be derived from or isolated from a fish, a bird, a mammal, a reptile, or an amphibian. For example, the fish calcitonin can include, but is not limited to salmon calcitonin (SEQ ID NO 1), eel calcitonin (SEQ ID NO 3), humpback salmon calcitonin (SEQ ID NO 8), ray fish salmon (SEQ ID NO 4), bastard halibut (or olive flounder calcitonin) (SEQ ID NO 9), sardine calcitonin (SEQ ID NO 7), goldfish calcitonin (SEQ ID NO 13), arctic charr calcitonin (SEQ ID NO 14), and atlantic salmon calcitonin (SEQ ID NO 15). The mammal calcitonin can include, but is not limited to, human calcitonin (SEQ ID NO 2), pig calcitonin (SEQ ID NO 5), dog calcitonin (SEQ ID NO 10), mouse calcitonin (SEQ ID NO 12) and bovine calcitonin. The bird calcitonin can include, but is not limited to, chicken calcitonin (SEQ ID NO 6). In some aspects, the calcitonin can include amino acid substitutions, deletions, or insertions. In yet another aspect, the calcitonin can be a synthetic construct. For example, (SEQ ID NO 11) is a synthetic construct. In some aspects, the synthetic construct can include, but is not limited to, recombinant calcitonin expressed from a cDNA of a vertebrate calcitonin or a product of a fusion gene. In some aspects, the synthetic construct can include amino acid insertions, deletions, or substitutions. In some aspects, either the full-length or a truncated portion of a cDNA derived from a vertebrate calcitonin can be spliced to cDNA of another gene to form a calcitonin fusion gene and ultimately expressed as a calcitonin fusion protein.

In some aspects, the peptide sequence can include the vertebrate calcitonin family including, but not limited to, calcitonin, calcitonin gene-related peptide (CGRP), alpha-CGRP, beta-CGRP, amylin (AMY), adrenomedullin (ADM; ADM1), adrenomedullin 2 (ADM1; intermedin), calcitonin receptor (CTR), calcitonin-like receptor (CLR), amylin receptor (AMY1, AMY2, AMY3), and receptor activity modifying proteins (RAMPs). In some aspects the compositions described herein can include peptides conjugated to targeting ligands using similar linkers, chemistry, and procedures described herein.

In some aspects, the calcitonin includes a peptide sequence at least 60% identical to SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, and SEQ ID NO 15. In some aspects, the calcitonin includes a peptide sequence at least 65% identical to SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, and SEQ ID NO 15. In some aspects, the calcitonin includes a peptide sequence at least 70% identical to SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, and SEQ ID NO 15. In another aspect, the calcitonin includes a peptide sequence at least 75% identical to SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, and SEQ ID NO 15. In another aspect, the calcitonin includes a peptide sequence at least 80% identical to SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, and SEQ ID NO 15. In some aspects, the calcitonin includes a peptide sequence at least 85% identical to SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, and SEQ ID NO 15. In some aspects, the calcitonin includes a peptide sequence at least 86% identical to SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, and SEQ ID NO 15. In some aspects, the calcitonin includes a peptide sequence at least 87% identical to SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, and SEQ ID NO 15. In some aspects, the calcitonin includes a peptide sequence at least 88% identical to SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, and SEQ ID NO 15. In some aspects, the calcitonin includes a peptide sequence at least 89% identical to SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, and SEQ ID NO 15. In some aspects, the calcitonin includes a peptide sequence at least 90% identical to SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, and SEQ ID NO 15. In some aspects, the calcitonin includes a peptide sequence at least 91% identical to SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, and SEQ ID NO 15. In some aspects, the calcitonin includes a peptide sequence at least 92% identical to SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, and SEQ ID NO 15. In some aspects, the calcitonin includes a peptide sequence at least 93% identical to SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, and SEQ ID NO 15. In some aspects, the calcitonin includes a peptide sequence at least 94% identical to SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, and SEQ ID NO 15. In another aspect, the calcitonin includes a peptide sequence at least 95% identical to SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, and SEQ ID NO 15. In some aspects, the calcitonin includes a peptide sequence at least 96% identical to SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11. SEQ ID NO 12, SEQ ID NO 13, SEQ ID NO 14, and SEQ ID NO 15. In some aspects, the calcitonin includes a peptide sequence at least 97% identical to SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, and SEQ ID NO 15. In some aspects, the calcitonin includes a peptide sequence at least 98% identical to SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, and SEQ ID NO 15. In some aspects, the calcitonin includes a peptide sequence at least 99% identical to SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, and SEQ ID NO 15. In yet another aspect, the calcitonin includes a peptide sequence having SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, and SEQ ID NO 15. In yet another aspect, the calcitonin is a peptide sequence having SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, and SEQ ID NO 15.

In some aspects, the peptide sequence includes at least one, two, three, four, five, six, seven, eight, nine, ten, eleven, twelve, thirteen, fourteen, fifteen, sixteen, seventeen, eighteen, nineteen, twenty, twenty one, twenty two, twenty three, twenty four, twenty five, twenty six, twenty seven, twenty eight, twenty nine, thirty, thirty one, thirty two, thirty three, thirty four, thirty five, thirty six, thirty seven, thirty eight, thirty nine, forty, forty one, forty two, forty three, forty four, forty five, forty six, forty seven, forty eight, forty nine, or fifty reactive amino groups (i.e., amino groups that are capable of forming covalent bonds or linkages). In some aspects, the peptide sequence can include from 1 to 500 reactive amino groups, from 1 to 400 reactive amino groups, from 1 to 300 reactive amino groups, from 1 to 200 reactive amino groups, from 1 to 100 reactive amino groups, or from 1 to 50 reactive amino groups. In this aspect, a linker is capable of independently covalently bonding to any reactive amino of the peptide sequence. In some aspects, the reactive amino groups include the N-terminus of the peptide, the R-group of lysine, the R-group of arginine, any amino acid containing a free reactive amino group or a combination thereof.

In some aspects, the peptide sequence includes an N-terminus. In some aspects, the peptide sequence includes at least one lysine residue and an N-terminus. In another aspect, the peptide sequence includes at least two lysine residues and an N-terminus. For example, the peptide sequence of SEQ ID NO 1 has an N-terminus and two lysine residues. In each of these aspects, a linker is capable of independently, covalently bonding to the N-terminus and/or lysine residue(s) of the peptide sequence. In one aspect, a linker can covalently bond to the N-terminus. In another aspect, if at least one lysine residue is present in the peptide sequence, the linker can covalently bond to the at least one lysine residue. In some aspects, if at least one lysine residue is present in the peptide sequence, the linker can independently, covalently bond to the at least one lysine residue and the N-terminus of the peptide. In another aspect, if at least two lysine residues are present in the peptide sequence, the linker can independently, covalently bond to the at least two lysine residues. In another aspect, if at least two lysine residues are present in the peptide sequence, the linker can independently, covalently bond to the at least two lysine residues and the N-terminus of the peptide sequence. In each aspect, if a lysine residue is present in the peptide sequence, the linker is capable of covalently bonding to at least one amine group of lysine (i.e., the R group, the N-terminus, or a combination thereof). When the peptide sequence is covalently bonded to a linker, a peptide linker intermediate is formed.

In some aspects, the peptide sequence includes an N-terminus. In some aspects, the peptide sequence includes at least one arginine residue and an N-terminus. In another aspect, the peptide sequence includes at least two arginine residues and an N-terminus. In yet another aspect, the peptide sequence includes at least one arginine residue, at least one lysine residue, and an N-terminus. In one aspect, a linker can covalently bond to the N-terminus. In another aspect, if at least one arginine residue is present in the peptide sequence, the linker can covalently bond to the at least one arginine residue. In some aspects, if at least one arginine residue is present in the peptide sequence, the linker can independently, covalently bond to the at least one arginine residue and the N-terminus of the peptide. In another aspect, if at least arginine lysine residues are present in the peptide sequence, the linker can independently, covalently bond to the at least two arginine residues. In another aspect, if at least two arginine residues are present in the peptide sequence, the linker can independently, covalently bond to the at least two arginine residues and the N-terminus of the peptide sequence. In each aspect, if a arginine residue is present in the peptide sequence, the linker is capable of covalently bonding to at least one amine group of arginine (i.e., the R group, the N-terminus, or a combination thereof). In some aspects, if at least one arginine is present and at least one lysine is present, the linker can independently, covalently bond to the at least one arginine residue, to the at least one lysine residue, and the N-terminus. When the peptide sequence is covalently bonded to a linker, a peptide linker intermediate is formed.

The linker as described herein can be hydrophilic, hydrophobic, amphiphilic, or any combination thereof. In one aspect, both hydrophilic and amphiphilic linkers are water soluble. In some aspects, the linkers described herein have at least one functional group or at least two functional groups capable of covalent bonding. In some aspects, the linkers described herein have at least two functional groups, one of which is capable of reacting with an amine or an amino group present in the peptide and the other functional group is capable of reacting with the bone targeting moiety. In one aspect, the linkers include a heterofunctional crosslinker or a homofunctional crosslinker. In this aspect, heterofunctional crosslinkers can include a linker having at least two different functional groups capable of covalent bonding. For example, the heterofunctional linker could have a thiol group located at one end of the linker and a carboxyl group at the opposite end of the linker. In this example, the linker may be illustrated as follows: HS-linker-COOH. In another aspect, the homofunctional crosslinkers include a linker having at least two identical functional groups capable of covalent bonding. For example, the homofunctional linker could have two thiol groups, one of which is located at one end of the linker and the other is located at the opposite end of the linker. In this example, the linker may be illustrated as follows: HS-linker-SH. For example, the linker has at least one group capable of reacting with a nucleophile. In this aspect, the nucleophile may covalently bond to the linker via a Michael addition. In this example, the linker possesses an olefinic group in conjugation with a carbonyl group. In another aspect, the peptide sequence and the linker can covalently bond via a primary amine reacting with a carboxyl group. In a further example, the linker has functional groups that can react with a thiol group.

In some aspects, the linker includes sulfosuccinimidyl-4-(N-maleimidomethyl)cyclohexane-1-carboxylate (Sulfo-SMCC) and derivatives thereof, m-maleimidobenzoyl-N-hydroxysulfosuccinimide ester (Sulfo-MBS) and derivatives thereof, 3-Maleimidobenzoyl-N-hydroxysuccinimide ester (MBS) and derivatives thereof, sulfosuccinimidyl 6-(3'-[2-pyridyldithio]-propionamido)hexanoate (Sulfo-LC-SPDP) and derivatives thereof, polyethylene glycol (PEG) and derivatives thereof, m-maleimidobenzoyl-N-hydroxysuccinimide ester and derivatives thereof, N-succinimidyl(4-iodoacetyl)aminobenzoate (SIAB), maleimido butryloxy-succinimide ester (GMBS) and derivatives thereof, N-(e-MaleimidoCaproyloxy)-N-HydroxySuccinimide ester (EMCS) and derivatives thereof, succinimidyl-6-((iodoacetyl)amino)hexanoate (SIAX) and derivatives thereof, Succinimidyl-4-(p-maleimidophenyl)butyrate (SMPB) and derivatives thereof, succinimidyl-4-(((iodoacetyl)amino)methyl)cyclohexane-1-carboxylate (SIAC) and derivatives thereof, p-nitrophenyl iodoacetate (NPIA) and derivatives thereof, or any combination thereof.

In some aspects, the linker includes, but is not limited to, a heterofunctional water soluble crosslinker wherein the hetero functional crosslinker is sulfosuccinimidyl-4-(N-maleimidomethyl)cyclohexane-1-carboxylate (Sulfo-SMCC) and derivatives thereof, m-maleimidobenzoyl-N-hydroxysulfosuccinimide ester (Sulfo-MBS) and derivatives thereof, 3-Maleimidobenzoyl-N-hydroxysuccinimide ester (MBS) and derivatives thereof, sulfosuccinimidyl 6-(3'-[2-pyridyldithio]-propionamido)hexanoate (Sulfo-LC-SPDP) and derivatives thereof, polyethylene glycol (PEG) and derivatives thereof including, but not limited to, a heterobifunctional PEG derivative containing an amine and a thiol reactive terminal functional groups, an acrylate-PEG-NHS, an acrylate-polymer-NHS, m-maleimidobenzoyl-N-hydroxysuccinimide ester and derivatives thereof, N-succinimidyl(4-iodoacetyl)aminobenzoate (SIAB) and derivatives thereof including N-succinimidyl(4-iodoacetyl)aminobenzoate (Sulfo-SIAB), maleimido butryloxy-succinimide ester (GMBS) and derivatives thereof including, but not limited to, m-MaleimidoButyryloxy-SulfoSuccinimide ester (Sulfo-GMBS), N-(e-MaleimidoCaproyloxy)-N-HydroxySuccinimide ester (EMCS) and derivatives thereof, including but not limited to, N-(e-MaleimidoCaproyloxy)SulfoSuccinimide ester (Sulfo-EMCS), succinimidyl-6-((iodoacetyl)amino)hexanoate (SIAX) and derivatives thereof, Succinimidyl-4-(p-maleimidophenyl)butyrate (SMPB) and derivatives thereof, succinimidyl-4-(((iodoacetyl)amino)methyl)cyclohexane-1-carboxylate (SIAC) and derivatives thereof, p-nitrophenyl iodoacetate (NPIA) and derivatives thereof, or any combination thereof.

In some aspects, the compositions described herein have only one linker. For example, as shown within the examples section and FIG. 1, that composition has mono-substituted, bi (or di)-substituted, and tri-substituted substituents all containing a Sulfo-SMCC linker. Therefore, in that aspect, only Sulfo-SMCC is the linker present in those mono-substituted, bi-substituted, and tri-substituted compositions. In yet another aspect, the compounds described herein may have multiple linkers. For example, the composition shown within the examples section can have two different linkers or three different linkers. In this aspect, a bi-substituted composition could have, for example, any two linkers described above. Therefore, a bi-substituted composition could have a PEG (or a PEG derivative) crosslinker covalently bonded to one amino acid present in the peptide sequence and a Sulfo-SMCC linker covalently bonded to another amino acid present in the peptide sequence. Likewise, the composition shown within the examples section can have three different linkers. In this aspect, a tri-substituted composition could have, for example, any three linkers described above. Therefore, a tri-substituted composition could have a PEG (or a PEG derivative) crosslinker covalently bonded to one amino acid present in the peptide sequence, a Sulfo-SMCC linker covalently bonded to another amino acid present in the peptide sequence, and a Sulfo-MBS linker covalently bonded to another amino acid present in the peptide sequence. Furthermore, this would contemplate compositions having at least 4, 5, 6, 7, 8, 9, 10, 11, 12, 13, 14, 15, 16, 17, 18, 19, or 20 amino acid residues present in the peptide sequence in which a linker could covalently bond.

The peptide linker intermediate as described herein can be reacted with a bone targeting moiety to form compounds having at least one peptide conjugated to at least one bone targeting moiety. The compositions described herein can include a bone targeting compound, wherein the bone targeting compound can include a bisphosphonate containing compound. In one aspect, bisphosphonate containing compound has the formula I

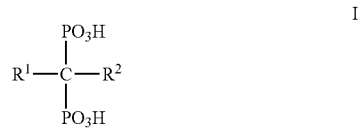

wherein $R^1$ and $R^2$ independently comprise hydrogen, a hydroxyl group, an alkyl group, an alkylene group, an amine group, a thiol group, an aryl group, a cycloalkyl group, or any combination thereof, or the pharmaceutically acceptable salt or ester thereof, and wherein $R^1$ or $R^2$ are covalently attached to the linker. In some aspects, $R^1$ and $R^2$ can independently include an alkyl amine, an alkyl thiol, an amine alkyl thiol, an alkyl thioether, an alkylene amine, an alkylene thiol, an amine alkylene thiol, or a combination thereof. In some aspects, $R^1$ is hydrogen and $R^2$ is alkylene thioether group. In some aspects, $R^1$ is hydrogen and $R^2$ is $(CH_2)_nSR^3$, wherein $R^3$ is an alkyl group, an alkylene group, an aryl group, a cycloalkyl group, an alkyl thiol group, an alkylene thiol group or any combination thereof, and n is from 1 to 8. In this aspect, $R^3$ is covalently attached to the linker. In some aspects, $R^1$ is hydrogen and $R^2$ is an amino alkyl thiol group. In some aspects, $R^1$ is hydrogen and $R^2$ is —$NR^3(CH_2)_nS$—, wherein $R^3$ is hydrogen or an alkyl group and n is from 1 to 8, and the linker is covalently bonded to sulfur. In some aspects, the bone targeting moiety comprises a residue of a thiol bisphosphonate compound.

In one aspect, the bisphosphonate containing compound includes, but is not limited to, a residue of etidronic acid, clodronic acid, tiludronic acid, pamidronic acid, neridronic acid, olpadronic acid, alendronic acid, ibandronic acid, zolendronic acid, risedronic acid, or a combination thereof. In some aspects, the bone targeting moiety is a residue of {2-[(3-mercaptopropyl)thio]ethane-1,1-diyl}bis(phosphonic acid). In this aspect, the targeting moiety is covalently attached to the linker via the sulfur atom.

In some aspects, the peptides described herein can be reacted with linkers to form peptide linker intermediates, and these intermediates can subsequently be reacted with at least one bone targeting moiety to form the desired composition or compound. For example, in some aspects, the peptide-linker-bone targeting moiety includes a composition wherein the peptide sequence is a salmon calcitonin peptide (SEQ ID NO 1), wherein the linker is a sulfosuccinimidyl-4-(N-maleimidomethyl)cyclohexane-1-carboxylate (Sulfo-SMCC), and the targeting moiety is {2-[(3-mercaptopropyl)thio]ethane-1,1-diyl}bis(phosphonic acid).

The term "PEGylation" refers to the conjugation or bonding of polyethylene glycol to the compositions described herein. In some aspects, polyethylene glycol can be used as a linker, as described above, to covalently link the peptide to the bone targeting moiety. In certain aspects, polyethylene glycol can covalently bond only to the peptide but not to the bone targeting moiety. In some aspects, polyethylene glycol can covalently bond to another linker wherein the other linker is covalently bonded to the peptide. In certain aspects, the compositions herein can be PEGylated to increase the molecular weight of a composition, to increase the half-life of a composition, and to decrease the immunogenicity of a composition. In each of these aspects, the compositions described herein can be PEGylated. In some aspects, PEGylation of these compositions can be advantageous. For example, PEGylation can increase the composition's solubility. In addition, PEGylation can increase the stability of calcitonin while decreasing calcitonin's tendency to aggregate. In some aspects, PEGylation can also decrease calcitonin's immunogenicity.

In some aspects, the bone targeting moiety described herein can be directly reacted and linked to the peptide. In this aspect, the peptide and bone targeting moiety are directly linked.

Any of the compounds described herein can be the pharmaceutically-acceptable salt or ester thereof. In one aspect, pharmaceutically-acceptable salts are prepared by treating the free acid with an appropriate amount of a pharmaceutically-acceptable base. Representative pharmaceutically-acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. In one aspect, the reaction is conducted in water, alone or in combination with an inert, water-miscible organic solvent, at a temperature of from about 0° C. to about 100° C. such as at room temperature. In certain aspects where applicable, the molar ratio of the compounds described herein to base used are chosen to provide the ratio desired for any particular salts. For preparing, for example, the ammonium salts of the free acid starting material, the starting material can be treated with approximately one equivalent of pharmaceutically-acceptable base to yield a neutral salt.

In another aspect, if the compound possesses a basic group, it can be protonated with an acid such as, for example, HCl, HBr, or $H_2SO_4$, to produce the cationic salt. In one aspect, the reaction of the compound with the acid or base is conducted in water, alone or in combination with an inert, water-miscible organic solvent, at a temperature of from about 0° C. to about 100° C. such as at room temperature. In certain aspects where applicable, the molar ratio of the compounds described herein to base used are chosen to provide the ratio desired for any particular salts. For preparing, for example, the ammonium salts of the free acid starting material, the starting material can be treated with approximately one equivalent of pharmaceutically-acceptable base to yield a neutral salt.

Ester derivatives are typically prepared as precursors to the acid form of the compounds. Generally, these derivatives will be lower alkyl esters such as methyl, ethyl, and the like. Amide derivatives —(CO)NH$_2$, —(CO)NHR and —(CO)NR)$_2$, where R is an alkyl group defined above, can be prepared by reaction of the carboxylic acid-containing compound with ammonia or a substituted amine.

In a further aspect, the peptides, linkers, and bone targeting moieties mentioned above can be used to make pharmaceutical compositions. The complexes described above can be administered to a subject using techniques known in the art. For example, pharmaceutical compositions can be prepared with the complexes. It will be appreciated that the actual preferred amounts of the complex in a specified case will vary according to the specific compound being utilized, the particular compositions formulated, the mode of application, and the particular situs and subject being treated. Dosages for a given host can be determined using conventional considerations, e.g., by customary comparison of the differential activities of the subject compounds and of a known agent, e.g., by means of an appropriate conventional pharmacological protocol. Physicians and formulators, skilled in the art of determining doses of pharmaceutical compounds, will have no problems determining dose according to standard recommendations (Physicians Desk Reference, Barnhart Publishing (1999).

Pharmaceutical compositions described herein can be formulated in any excipient the biological system or entity can tolerate. Examples of such excipients include, but are not limited to, water, saline, Ringer's solution, dextrose solution, Hank's solution, and other aqueous physiologically balanced salt solutions. Nonaqueous vehicles, such as fixed oils, vegetable oils such as olive oil and sesame oil, triglycerides, propylene glycol, polyethylene glycol, and injectable organic esters such as ethyl oleate can also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosol, cresols, formalin and benzyl alcohol.

Pharmaceutical carriers are known to those skilled in the art. These most typically would be standard carriers for administration to humans, including solutions such as sterile water, saline, and buffered solutions at physiological pH.

Molecules intended for pharmaceutical delivery can be formulated in a pharmaceutical composition. Pharmaceutical compositions can include carriers, thickeners, diluents, buffers, preservatives, surface active agents and the like in addition to the molecule of choice.

The pharmaceutical composition can be administered in a number of ways depending on whether local or systemic treatment is desired, and on the area to be treated. Administration can be topical, including ophthalmic and intranasal, or administration may be intravenous or intraperitoneal.

Preparations for administration include sterile aqueous or non-aqueous solutions, suspensions, and emulsions. Examples of non-aqueous carriers include water, alcoholic/aqueous solutions, emulsions or suspensions, including saline and buffered media. Parenteral vehicles, if needed for collateral use of the disclosed compositions and methods, include sodium chloride solution, Ringer's dextrose, dextrose and sodium chloride, lactated Ringer's, or fixed oils. Intravenous vehicles, if needed for collateral use of the disclosed compositions and methods, include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like can be necessary or desirable.

Dosing is dependent on severity and responsiveness of the condition to be treated, but will normally be one or more doses per day, with course of treatment lasting from several days to several months or until one of ordinary skill in the art determines the delivery should cease. Persons of ordinary skill can easily determine optimum dosages, dosing methodologies and repetition rates.

2. Methods for Making Compositions:

Further described herein are methods of making the compositions having a peptide linked to a bone targeting moiety. The method generally involves reacting at least one amine group present in a peptide sequence with at least one linker to form a peptide linker intermediate, and reacting the peptide linker intermediate with a bisphosphonate containing compound.

In this method any combination of the peptides, linkers, and bone targeting moieties described above can be used. For example, the peptide sequence used in this method can include salmon calcitonin, human calcitonin, pig calcitonin, eel calcitonin, ray fish calcitonin, bovine calcitonin, bovine calcitonin, chicken calcitonin, rat calcitonin, mouse calcitonin, bastard halibut or olive flounder calcitonin, dog calcitonin, sardine calcitonin, humpback salmon calcitonin, or any combination thereof.

In some aspects, the peptide sequence used in this method can include a sequence at least 90% identical to SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, and SEQ ID NO 15.

In some aspects, the linker comprises a heterofunctional water soluble crosslinker For example, the linker used herein can include sulfosuccinimidyl-4-(N-maleimidomethyl)cyclohexane-1-carboxylate (Sulfo-SMCC) and derivatives thereof, m-maleimidobenzoyl-N-hydroxysulfosuccinimide ester (Sulfo-MBS) and derivatives thereof, 3-Maleimidobenzoyl-N-hydroxysuccinimide ester (MBS) and derivatives thereof, sulfosuccinimidyl 6-(3'-[2-pyridyldithio]-propionamido)hexanoate (Sulfo-LC-SPDP) and derivatives thereof, polymer and derivatives, polyethylene glycol (PEG) and derivatives thereof including, but not limited to, a heterobifunctional PEG derivative containing an amine and a thiol reactive terminal functional groups, an acrylate-PEG-NHS, an acrylate-polymer-NHS, m-maleimidobenzoyl-N-hydroxysuccinimide ester and derivatives thereof, N-succinimidyl (4-iodoacetyl)aminobenzoate (SIAB) and derivatives thereof including N-succinimidyl(4-iodoacetyl)aminobenzoate (Sulfo-SIAB), maleimido butryloxy-succinimide ester (GMBS) and derivatives thereof including, but not limited to, m-MaleimidoButyryloxy-SulfoSuccinimide ester (Sulfo-GMBS), N-(e-MaleimidoCaproyloxy)-N-HydroxySuccinimide ester (EMCS) and derivatives thereof, including but not limited to, N-(e-MaleimidoCaproyloxy)SulfoSuccinimide ester (Sulfo-EMCS), succinimidyl-6-((iodoacetyl)amino) hexanoate (SIAX) and derivatives thereof, Succinimidyl-4-(p-maleimidophenyebutyrate (SMPB) and derivatives thereof, succinimidyl-4-(((iodoacetyl)amino)methyl)cyclohexane-1-carboxylate (SIAC) and derivatives thereof, p-nitrophenyl iodoacetate (NPIA) and derivatives thereof, or any combination thereof.

In this method, the bone targeting moiety can include any of the bisphosphonate compounds described above. For example, the bisphosphonate compound can include a thiol containing bisphosphonate compound.

The amount of linker used relative to the peptide will determine the number of linkers attached to the peptide. For example, a particular ratio, for example a mol/mol ratio, of the peptide sequence to linker can be utilized to form a peptide linker intermediate. In addition, reaction times can be adjusted to form various peptide linker intermediates that can include mono-substituted, bi-substituted, and tri-substituted peptide linker intermediates as shown within the example section. In this aspect, the ratio of the peptide sequence to linker can include but is not limited to a 1:3, a 1:5, a 1:7, or a 1:10 mol/mol ratio. In certain aspects, the ratio of the peptide sequence to linker is a 1:5 mol/mol ratio. In some aspects, the peptide sequence and linker(s) are reacted for a period of time including, but not limited to, 1, 2, 3, 4, 5, 10, 15, 20, 25, 35, 40, 45, 50, 60, 65, 70, 75, 80, 85, or 90 minutes at about room temperature to form the peptide linker intermediate.

In some aspects, when the peptide sequence and linker(s) are reacted, organic solvents, organic solvents mixed with aqueous solvents including buffers, or any combination thereof can be added. Organic solvents can include, but are not limited to, dimethyl sulfoxide (DMSO), trimethylformamide (TMF), dimethylformamide (DMF), chloroform, triethylamine (TEA), and alcohols. In some aspects, the organic solvent can be added to the reaction at a 0.01% v/v, 0.02% v/v, 0.03% v/v, 0.04% v/v, 0.05% v/v, 0.1% v/v, 0.2% v/v, 0.3% v/v, 0.4% v/v, 0.5% v/v, 0.6% v/v, 0.7% v/v, 0.8% v/v, 0.9% v/v, 1.0% v/v, 1.5% v/v, 2.0% v/v or more final concentration of the organic solvent. Aqueous solvents and buffers can include, but are not limited to, water, phosphate buffers, carbonate buffers, and acetate buffers. In one aspect, triethylamine (TEA) can be used. In some aspects, the overall final concentration of TEA can include but is not limited to 0.1% v/v. In another aspect, TEA in dimethylformamide can be used.

In some aspects, either when reacting the peptide sequence and linkers (i.e., during the formation of the peptide linker intermediate) or after the formation of the peptide linker intermediate, the pH can be adjusted. In some aspects, the pH should be alkaline, wherein the pH ranges from 6.0 to 14.0, 7.0 to 14.0, from 7.0 to 12.0, from 7.0 to 10.0, from 7.0 to 9, from 7.0 to 8.0, or from 7.5 to 8.0. In certain aspects, the pH is from 7.0 to 9. In some aspects, when TEA is present, it acts as an organic PH modifier to make the pH more alkaline.

After the formation of the peptide linker intermediate, the peptide linker intermediate can be reacted with a bone targeting moiety, which includes a thiol containing bisphosphonate compound, to form at least one of the compositions described herein. In some aspects, a particular ratio, for example a mol/mol ratio, of the peptide linker intermediate to bone targeting moiety can be utilized to form one of the compositions described herein. In addition, reaction times can be adjusted to form various peptide-linker-bone targeting moiety compositions that can include mono-substituted, bi-substituted, and tri-substituted compositions. In this aspect, the ratio of the peptide linker intermediates to bone targeting moiety can include but is not limited to a 1:3, a 1:5, a 1:7, a 1:10, or a 1:20 mol/mol ratio. In this reaction, reaction times can be adjusted to form various substituted peptide-linker-bone targeting moiety compositions. In some aspects, the peptide linker intermediate is reacted with a bone targeting moiety, which can include a bisphosphonate containing compound, for 1 minute to 24 hours (or longer if desired) at room temperature if desired to form a peptide-linker-bone targeting moiety composition. In certain aspects, the reaction temperature may be cooler or warmer than room temperature if desired. In certain aspects, a longer reaction time may be desired, and the peptide linker intermediate is reacted with the bone targeting moiety at different times and different temperatures. For example, if a longer reaction time is desired, the peptide linker intermediate can be reacted with the bone targeting moiety for 1 to 2 hours at room temperature and then stored at 4° C. for up to 22 hours.

In some aspects, either when reacting the peptide linker intermediate with the bone targeting moiety (i.e., during the formation of the peptide linker intermediate) or after the formation of the peptide conjugated to a bone targeting moiety by a linker, the pH can be adjusted. In some aspects, buffers including, but not limited to, phosphate buffers, acetate buffers, or a combination thereof can be added. In some aspects, the pH can be adjusted to a pH ranging from 6.0 to 8.5, from 6.5 to 7.5, from 6.5 to 7.5, or from 6.5 to 7.0. In some aspects, the pH can be adjusted to pH 6.8.

Additional, non-limiting, procedures for making the compositions described herein are provided in the examples section and the figures.

3. Methods of Using Compounds Having Peptides Conjugated to Bone Targeting Moieties:

In some aspects, the compositions described herein can be administered to a subject to treat or prevent a condition that causes loss of bone mass. The subject can either be experiencing bone loss or be at risk for such a condition. To determine whether a subject is experiencing bone loss, numerous tests, such as bone density testing, a battery of genetic tests, a subject's medical history, and the subject's family medical history, can be used to make this determination. In one aspect, these compositions are administered to a subject, wherein the subject includes a mammal. In this aspect, the subject can include a human.

In certain aspects, the condition may be linked to congenital conditions or improper diet. In this aspect, an osteoclast may remove bone tissue (i.e., bone resorption) more quickly than new bone cells and tissue can be produced. The overall effect leads to osteoclast mediated resorptive bone loss. In some aspects, the condition includes, but is not limited to, osteoporosis, Paget's disease, osteolytic tumors, Rheumatoid Arthritis, Psoriatic Arthritis, Ankylosing Spondylitis, Osteoarthritis, hypercalcemia, osteopenia including drug induced osteopenia, or a combination thereof. In some aspects, the condition causes osteoclast mediated resorptive bone loss.

In certain aspects, bone loss can be reduced by contacting the bone with the compositions described herein. In other aspects, the compositions described herein can be administered to a subject to prevent bone fractures and to strengthen bones.

In each of these aspects, administration may be via oral administration, injection including intramuscular or subcutaneous injection, or via nasal administration.

In some aspects, the subject would benefit from the administration of the compositions described herein because of the increased targeting and localization of the composition, which includes calcitonin, to bone and the increased retention time of the composition, which includes calcitonin, in and/or on the bone. This increased localization and retention time (i.e., enhanced drug delivery) could result in additional positive effects such as increasing bioavailability of calcitonin to bone cells, administering lower dosages of the peptide bisphosphonate conjugate when compared to administering calcitonin or bisphosphonate drugs alone, improved inhibition or reduction of osteoclast mediated resorptive bone loss when compared to administering calcitonin alone, and reducing the side-effects associated with administering calcitonin or bisphosphonate drugs alone.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

A novel bone targeting CT compound, containing from one to three water-soluble bone targeting moieties (thiol-BPs) was designed and synthesized. CT chemically coupled to a bisphosphonate can be effectively delivered to bone due to the high affinity of the bisphosphonate to bind bone. Following drug delivery to bone, any gradual hydrolysis of the conjugate to liberate free CT could also be of further clinical utility, as the CT would be released into the immediate bone microenvironment at its preferred site of action.

I. Synthesis and Evaluation of a Bioactive, Bone-Targeting Salmon Calcitonin Analogue Materials Salmon calcitonin was purchased from Calbiochem, USA and the sulfosuccinimidyl-4-[N-maleimidomethyl]cyclohexane-1-carboxylate (Sulfo-SMCC) was from Molecular Biosciences, USA. Thiol functionalized Bisphosphonate (Thiol-BP) was purchased from Surfactis Technologies Inc, France. HPLC grade water, Dimethyl Sulfoxide (DMSO) and Triethylamine (TEA) were from Sigma-Aldrich (Saint Louis, Mo., USA).

Methods and Results

Synthesis of Bone Targeting sCT Analogue sCT was reacted with sulfo-SMCC in DMSO in 1:3 molar ratio for 45 minutes at room temperature to generate functionalized thiol reactive sCT analogue, which were added intermittently with constant stirring to Thiol-BP solution in 100 mM phosphate buffer (PB) pH 6.8 in 1:20 mol/mol ratio and reacted for 2 h at room temperature in dark. Intermediates and final products in each steps were confirmed by matrix-assisted laser desorption ionization time-of-flight mass spectrometer (MALDI-TOF).

Unreacted BP and SMCC were removed by dialysis (MWCO 1000 D, Spectrum Laboratory, USA) against 20 mM Sodium Acetate buffer pH 5 (3× every 3 hours, 5× every 12 hours). Finally, the amount of sCT in sCT-BP conjugates was determined by Micro BCA protein assay. Briefly, an aliquot of 100 μl suitably diluted sample was mixed with 100 μl of working reagent (micro BCA reagent A, B and C in a volume ratio of 50:48:2). The mixture was incubated at 37° C. for 2 h and then cooled down to room temperature. Absorbance at 562 nm was measured using 96-well microplate reader. The amount of sCT was calculated by converting the absorbance into mass using the standard curve.

Possible reaction products of sCT with sulfo-SMCC are shown in FIG. 1. sCT has three primary amines at Lys 11, Lys 18 and N-terminal, which can react with the NHS functional group of sulfo-SMCC to generate three intermediate conjugates: mono-, di- and tri-substituted thiol reactive sCT analogues. The MALDI-TOF spectra of sCT showed a peak at 3433.721 D. Other peaks represent either impurities or degradation products during analysis. When sCT reacts with sulfo-SMCC (MW 436.37 D), sulfosuccinimidy group with MW 217.13 is lost and N-maleimidomethyl)cyclohexane-1-carboxylate group with MW 219.24 D forms stable amide bond with sCT amine functional group to give sCT-SMCC intermediates with theoretical molecular weights of 3651.96, 3870.2 and 4089.44 D for mono, di and tri substitution. They respectively appeared at 3656.640, 3875.790 and 4096.214 m/z using undialyzed reaction mixture. Based on peak intensity and area, formation of formation of di and tri-substituted products was favorable over mono substitution. However, the formation of di-substituted favored over tri-substituted. Loss of sCT peak and the appearance of new peaks closer to theoretical mass suggested that the reaction was complete.

Expected reaction products of functionalized sCT with Thiol-BP (MW: 294.963) are shown in FIG. 1. MALDI-TOF results of sCT-BP conjugates using 100 mM pH 6.8 Sodium Phosphate buffer were obtained. A peak at 4172.825 was for sCT-2SMCC-1BP whose theoretical m/z was 4170.753. sCT-2SMCC-2BP appeared at 4470.085 (theoretical m/z 4465.716), sCT-3SMCC-2BP was seen at 4689.534 (theoretical m/z 4686.14) and sCT-3SMCC-3BP appeared at 4985.912 (theoretical m/z 4981.103). We did not see a peak for sCT-1SMCC-1BP after second step reaction.

Determination of Secondary Structure of sCT Analogue by Circular Dichroism

For a more detailed analysis of the influence of BP coupling on secondary structural confirmation of sCT, the circular dichroism (CD) spectrum of sCT, sCT-SMCC and sCT-BP was measured in the 20 mM acetate buffer pH 5.0. CD spectra were obtained with a ConvCD spectrophotometer instrument. Spectra were acquired over a wavelength range of 190 to 260 nm. The $N_2$ flow rate was set at 5 l/min. The sample cuvette was cleaned with 20 mM Sodium Acetate buffer pH 5, and the spectra of test samples, which comprised of 400 µg/mL of sCT or equivalent the same buffer, were recorded with the corresponding buffer serving as blanks.

Figure 2:
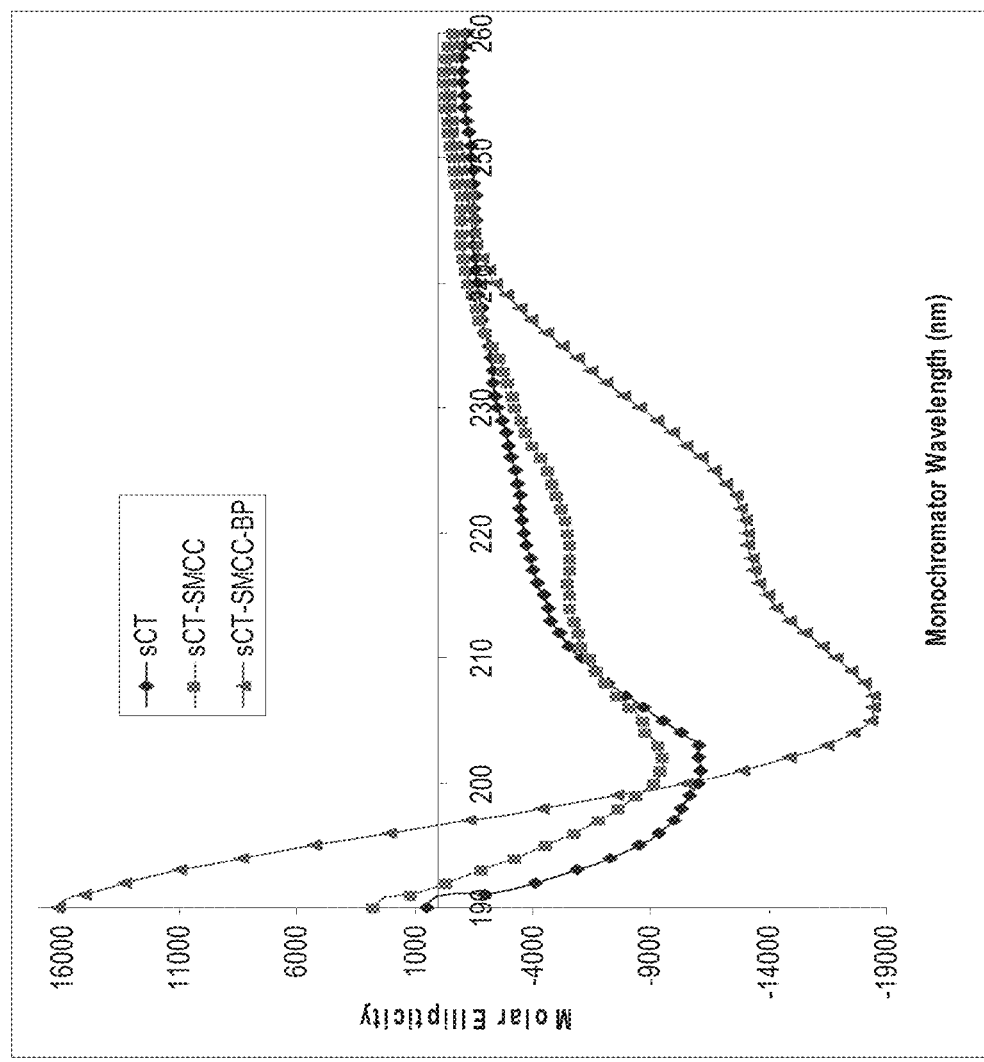
FIG. 2 shows the circular dichroism spectra of sCT, sCT-SMCC and sCT-BP to determine the effect of SMCC or SMCC-BP conjugation on sCT secondary structural confirmation.

The circular dichroism (CD) spectrum of sCT (FIG. 2) shows a minimum at around 200 nm, indicating that the peptide assumed a random coil conformation. sCT has very little helical content as demonstrated by the low magnitude of the ellipticity at 222 nm. The shape of the CD curve of sCT-SMCC and sCT-BP shows increased peak intensity at 222 nm and the peak at 200 was retained. In addition a positive peak appeared at below 200 nm indicating the tendency of SMCC to shift sCT secondary structure toward relatively more stable and less aggregation prone helical structure. CD spectra of sCT-BP in the same solvent displayed strong δ-helical character as shown by the presence of a positive peak at 198 and intense negative peaks at 208 and 222 nm. This is the first report of such helical structure in sCT using BP. As shown in later experiments, BP coupling had no adverse effect in receptor binding and bioactivity of sCT. In context of unaltered activity, shifting of sCT structure toward helical shape is highly desirable.

Cytotoxycity of sCT Analogue on Osteoclast Precursor Bone Marrow RAW 264.7 Cells RAW 264.7 cells (ATCC VA, USA) were seeded on 96 well plates at an initial density of $2 \times 10^4$ cells/well and incubated in 200 µl GIBCO High Glucose 1× Dulbecco's Modified Eagle Medium (DMEM) (Invitrogen CA, USA) supplemented with 4.5 g/L D-Glucose, L-Glutamine, 110 mg/L Sodium Pyruvate, 10% heat inactivated fetal bovine serum (FBS) and 1% Penicillin-Streptomycin (10000 U/mL; Invitrogen) in a Thermo Fisher Scientific Water Jacketed $CO_2$ incubator (37° C., 5% $CO_2$).

After 72 hrs, media was replaced by 200 µl basic DMEM media without FBS and incubated for 30 minutes. Then the media was replaced by 100 µl basic DMEM media containing sCT, sCT-SMCC and sCT-BP equivalent to 100, 500 and 1000 nM final sCT concentration and the cells were incubated for 4 hrs at 37° C. sCT containing media was then replaced by 100 µl basic media containing (3-[4,5-dimethylthiazol-2-yl]-2,5-diphenyl tetrazolium bromide) (MTT) at a concentration of 100 µg/well and incubated for another 4 hrs at 37° C. After removing the supernatant and washing twice with phosphate buffer saline, purple formazan crystals formed were dissolved in 200 µl solubilization solution (in vitro toxicology assay kit, # TOX-1, Sigma Aldrich, St. Louis, USA) and the absorbance was measured at 570 nm using microplate reader. Experiment was performed for n=8 and the absorbance of wells containing cells without sCT treatment was considered as 100% viable and used to calculate the relative viability of sCT treated cells.

Figure 3:
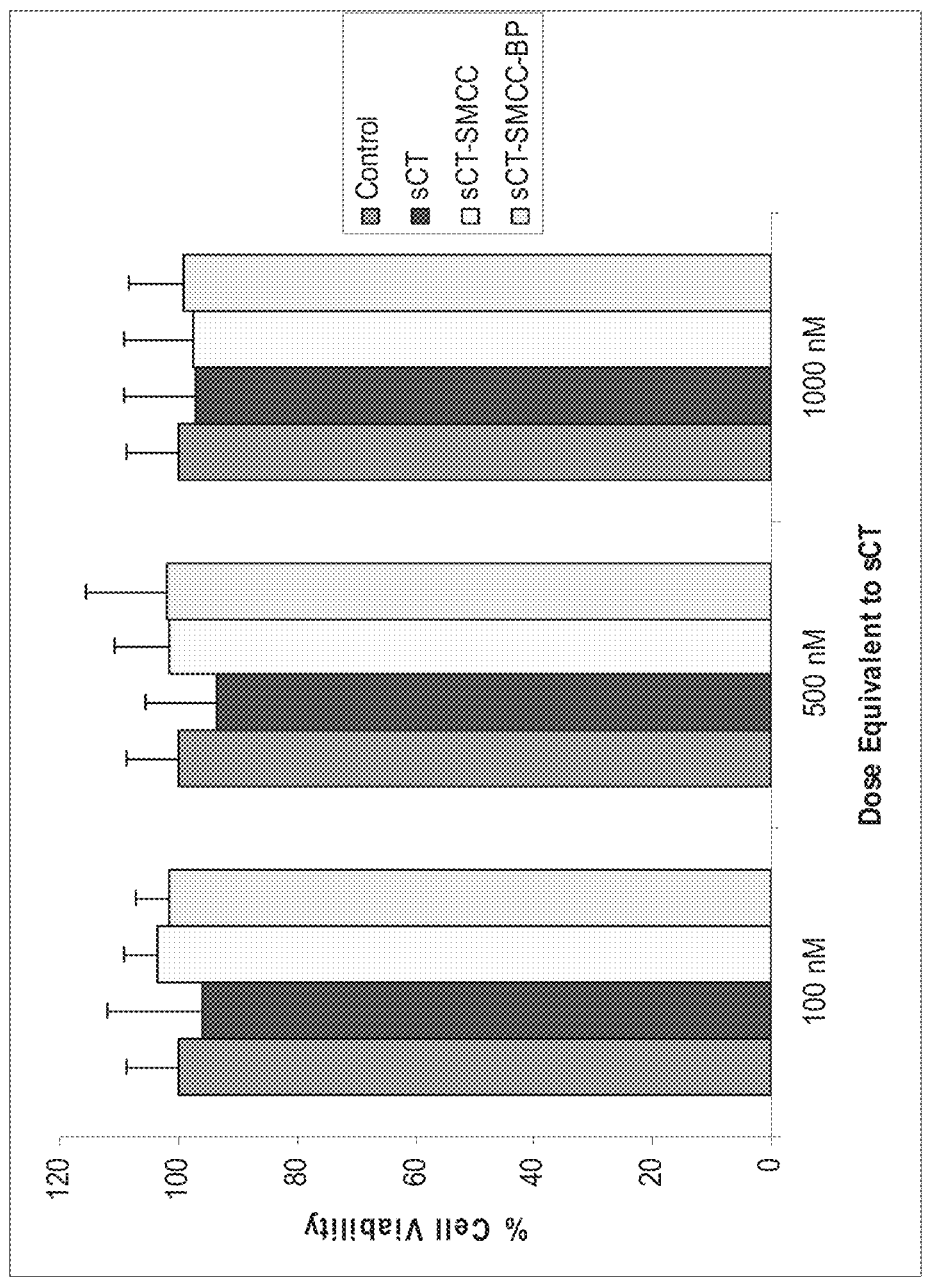
FIG. 3 shows the in vitro cytotoxycity of sCT analogue on osteoclast precursor bone marrow RAW 264.7 cells determined by MTT assay. 20000 Raw cell/well in 96 well plate (n=8) were cultured for 3 days and treated with sCT or equivalent followed by incubation at 37° C. for 4 hours in basic DMEM media. Cells were then treated with 100 µg/well MTT in basic DMEM media and the absorbance of formazan crystal solution was measured spectrometrically at 570 nm.

In MTT assay, mitochondrial dehydrogenases of viable cells cleave the tetrazolium ring of MTT yielding purple formazan crystals which are insoluble in aqueous solutions. They were dissolved in acidified isopropanol and the resulting purple solution was measured spectrophotometrically. An increase or decrease in cell number results in a concomitant change in the amount of formazan formed, indicating the degree of cytotoxicity caused by the test material. sCT and sCT analogues showed low levels of cytotoxicity as measured by the absorbance of formazan solution, compared to that seen with untreated media (FIG. 3). In all in vitro and in vivo bioactivity assays the maximum concentration used was equivalent to 100 nM sCT. However, cytoxicity was determined for the concentration up to 1000 nM sCT or equivalent. Even at the highest concentration tested, there was no significant difference in the viability of these cells Determination of Anti-Calcitonin Antibody Epitope and Bone Calcium Binding Specificity of sCT Analogue by ELISA sCT or sCT analogues equivalent to 1 µg/well were added in Calcium Phosphate coated Osteoclast Activity Assay Substrate plate (OCT USA, Inc.) in duplicate and the binding of BP to the calcium phosphate was allowed for 1 hours in the presence of 100 µl 100 mM Sodium Phosphate buffer pH 7. Plates were then washed three times with the same buffer containing 0.05% v/v Tween 80 (PBST). To avoid nonspecific binding, the wells were incubated with 3% w/v Bovine Serum Albumin for 1 h at room temperature. After washings, the wells were incubated with 100 µl of 1:5000 diluted rabbit anti-salmon calcitonin primary antibodies (US Biologicals, USA) for 1 h at room temperature. The wells were then washed three times with PBST and the bound antibodies were then incubated with secondary antibody, 1:5000 diluted goat anti-rabbit IgG conjugated with horseradish peroxidase (GAM-HRPO), for 1 h at room temperature. After final washings, 100 µl of 3,3',5,5'-tetramethylbenzidine (TMB substrate) was added to each well and incubated for 15 min at room temperature. The optical density (OD) was measured at 650 nm using an ELISA Vmax kinetic microplate reader (Molecular Devices Corp., California, and USA).

Figure 4:
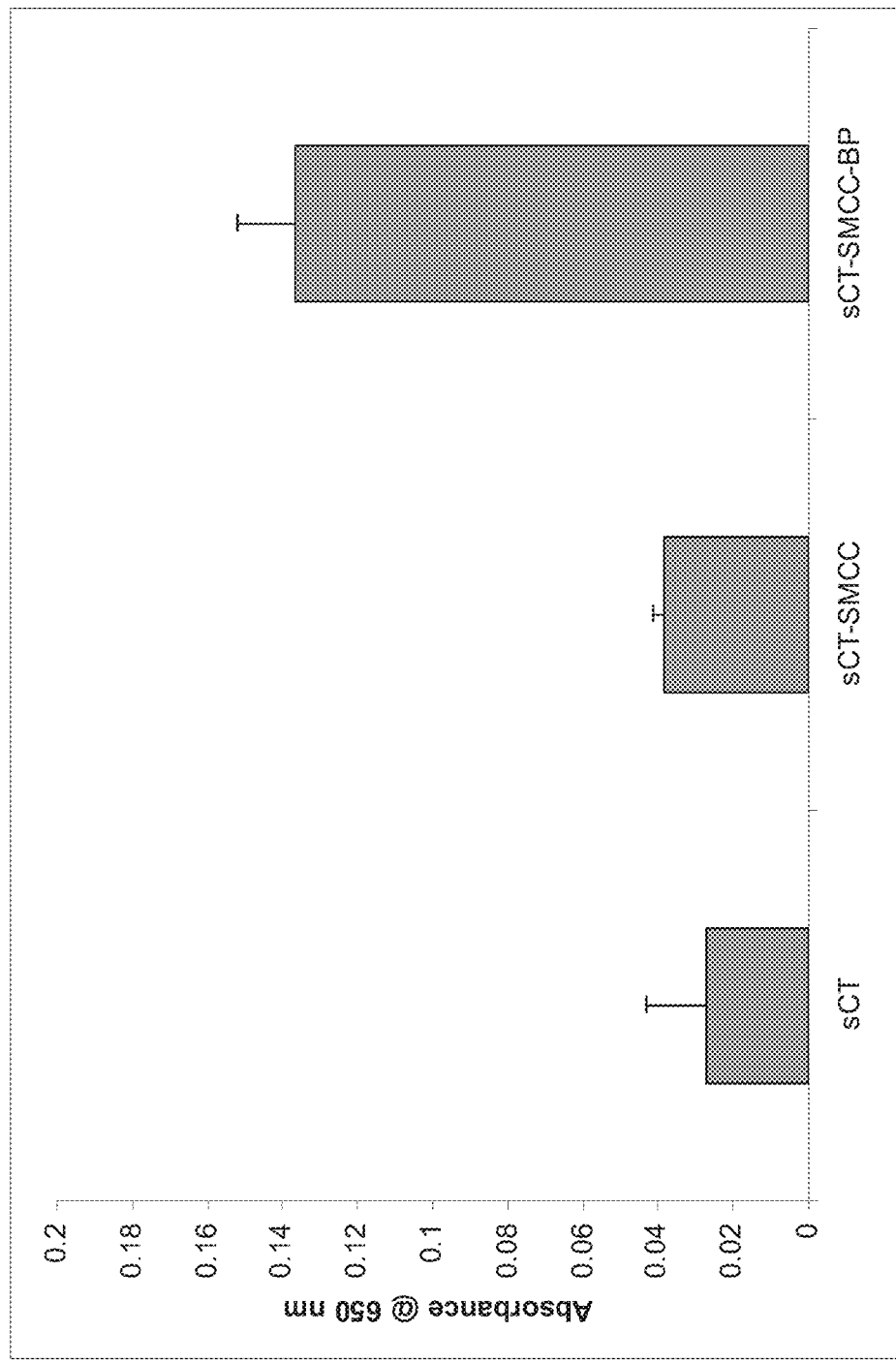
FIG. 4 shows the determination of anti-calcitonin antibody epitope binding specificity of sCT analogue by ELISA. Osteologic plate coated with calcium phosphate was incubated with sCT or equivalent (1 µg) in 100 µl 100 mM Phosphate buffer pH 7 for 1 hr, washed, blocked by BSA. Plates were then incubated with rabbit anti-sCT antibody followed by goat anti-rabbit IgG. TMB substrate was added and the absorbance of the developed color was measured at 650 nm.

FIG. 4 represents the result of anti-calcitonin antibody epitope binding specificity of sCT analogue by ELISA. BP in conjugates binds to calcium phosphate in osteologic plates leaving free sCT, which binds to its specific rabbit anti-salmon calcitonin antibody. Which was then detected using HRPO conjugated goat anti-rabbit IgG as a secondary antibody and TMB substrate. The absorbance of sCT-BP was 5 times higher than that of native sCT and sCT-PEG, suggesting the affinity of conjugates for the bone surface calcium and unaltered antibody epitope binding potential of sCT in them. However, absence of bone binding BP in sCT or sCT-PEG did not allow them to bind to calcium in these plates and were not significantly detected in subsequent ELISA. As the systemically administered sCT is 40% serum albumin bound in circulation, the small absorbance in sCT or sCT-PEG could be explained by their non specific binding with bovine serum albumin used as a blocking agent.

Calcitonin Receptor Binding Affinity and In Vitro Bioactivity of sCT-Analogue

T47D cells were cultured in triplicate in RPMI-1640 culture medium containing 1% penicillin-streptomycin, 10% fetal bovine serum, and insulin at final concentration of 0.2 IU/mL. Cells were seeded on 48 well plates at an initial density of $5 \times 10^4$ cells/well and incubated in 95% air and 5% $CO_2$ at 37° C. for 2 days. Cells were then washed with Hank's balanced salt solution (HBSS) and incubated in RPMI-1640 culture medium devoid of FBS, insulin and antibiotics for 30 minutes. Cells were then dosed with phosphodiesterase inhibitor, 3-isobutyl-1-methyl-xanthine (IBMX, 1 mM) and incubated at 37° C. for 30 min. 0, 10, 50 and 100 nM of sCT or equivalent sCT analogues were then added to the cells and incubated for 20 min at 37° C.

After removing the supernatant, cells were washed three times in cold phosphate buffer saline and resuspended in 500 µl of Cell Lysis Buffer. Cells were frozen at −30° C. and thawed with gentle mixing. The freeze/thaw cycle was repeated three times and the mixture was centrifuged at 600 g for 10 minutes at 2-8° C. to remove cellular debris. The supernatant was collected and stored at −30° C. cAMP concentrations were then measured using the cAMP Enzyme Immuno-Assay (EIA) kit (KGE002B, R & D systems, USA). Increased cAMP production in response to the different forms of sCT was calculated using a calibration curve constructed using standard cAMP. Values of cAMP concentration for native sCT was considered 100% for respective dosing and % change in cAMP concentration by equivalent sCT analogue relative to that of unmodified sCT was calculated.

Figure 5A:
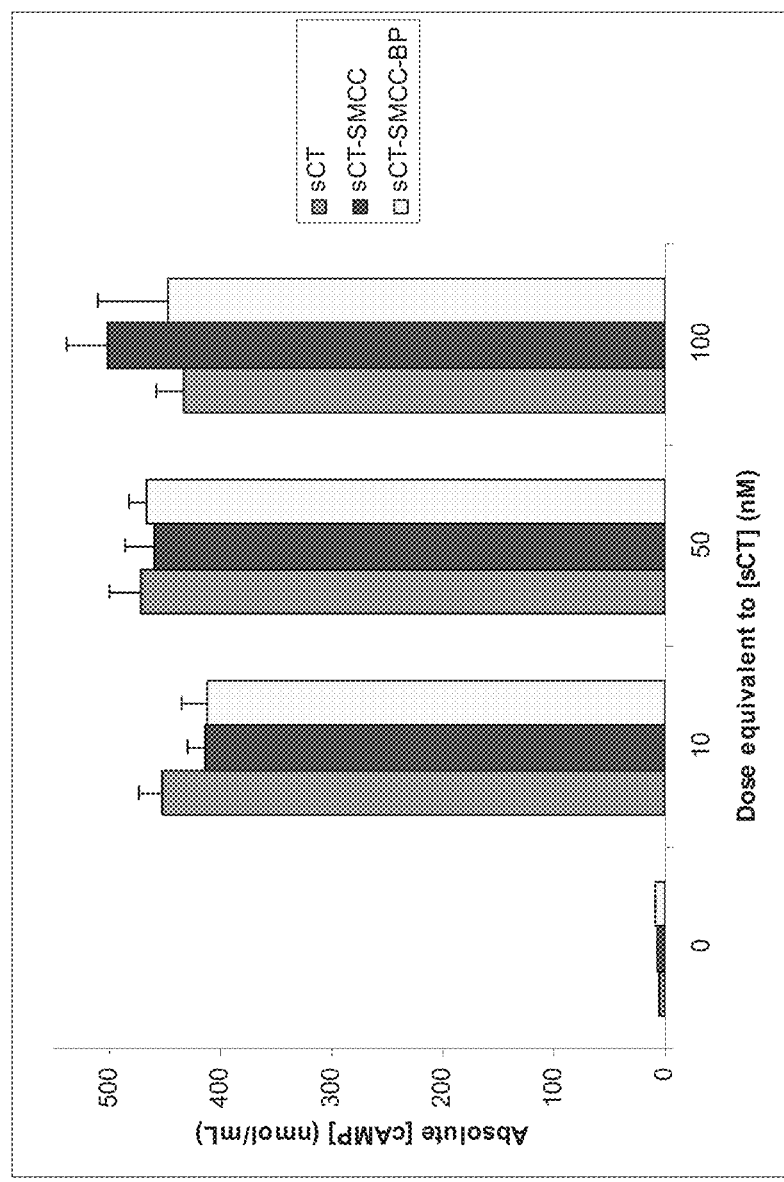
FIG. 5 shows the calcitonin receptor binding affinity and in vitro bioactivity sCT-analogue determined using intracellular cAMP stimulation in human T47D cells. 100000 cells/well were cultured for 2 days in 48 well plates in RPMI 1640 containing insulin. Phosphodiasterase activity was blocked using 3-IBMX and the cells were then treated with 0, 10, 50 and 100 nM sCT or equivalent. Generated cAMP was assayed by cAMP ELISA. (a) Absolute amount of cAMP (nmole/ml) and (b) cAMP (% maximal) as determined by considering the amount of cAMP generated by sCT for a particular concentration as 100%.
Figure 5B:
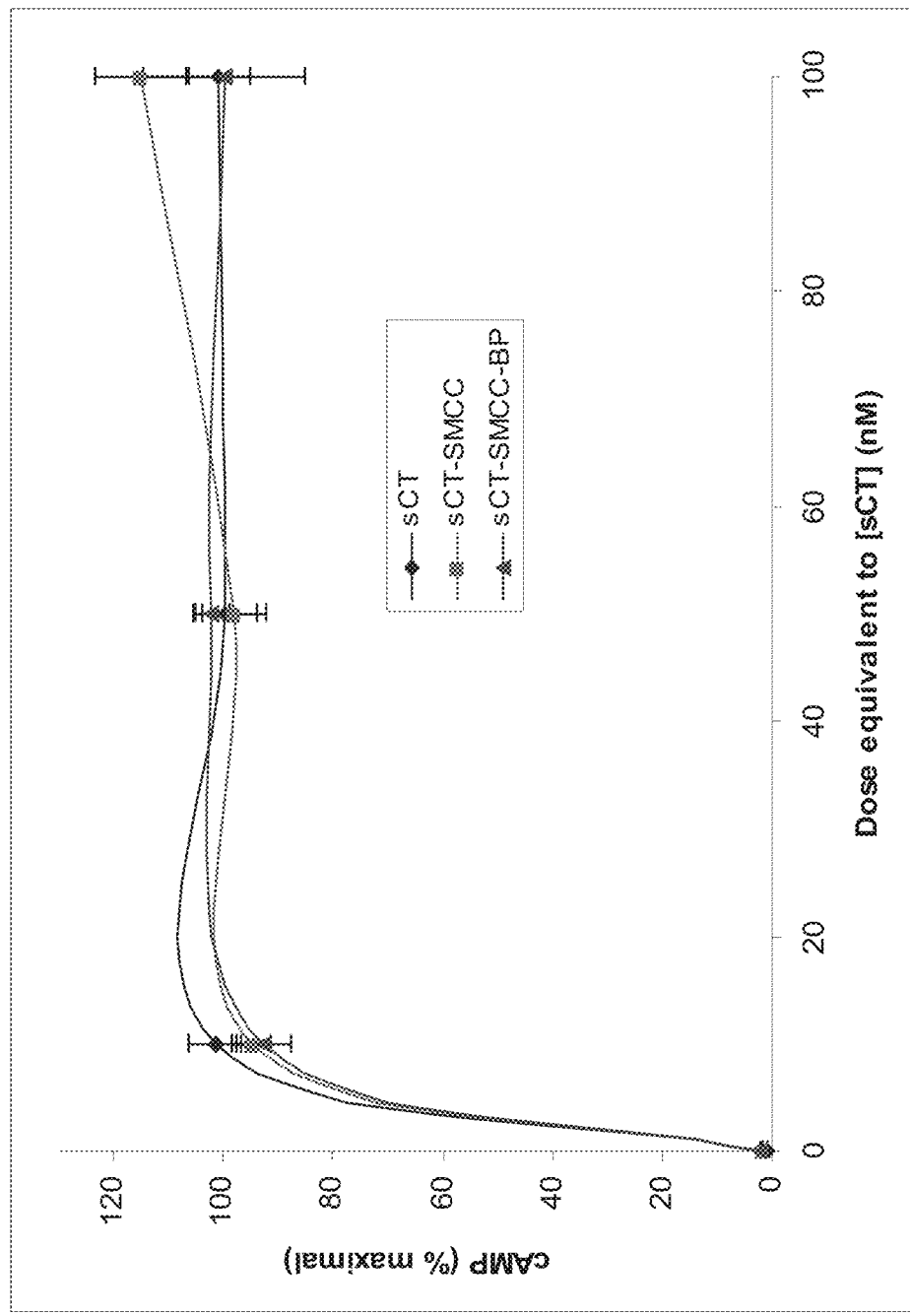

The ability for native sCT, sCT-SMCC, and sCT-BP to bind to CTR to generate intracellular cAMP in the presence of a phosphodiesterase inhibitor is shown in FIG. 5. The absolute amount of cAMP generated is shown in FIG. 5(a) and the intracellular cAMP generating activities of sCT analogues compared to sCT is on FIG. 5(b). In comparison to native sCT, at 10 mM concentration, sCT-SMCC and sCT-BP retained 94.3 and 92.8% sCT activity. Similarly, 98.05% and 101.98% activity was seen at 50 nM concentration, and 114.89% and 99.78% at 100 nM. Since the antiresorptive effects of calcitonin are mediated by calcitonin receptor found primarily in bone-resorbing osteoclast cells (OC), retention of sCT activity by sCT-BP can be therapeutically significant as it has the potential to be selectively deposited in bone after systemic administration.

In Vivo Bioactivity Assay: Effect of sCT Analogue on Plasma Calcium and Phosphate Levels in Normal Rats Pharmacodynamic response of sCT analogue was evaluated by analyzing plasma calcium concentration in the rat model. Sprague Dawley female rats weighing 230-260 g (about 6 weeks old) were purchased from Charles River, USA and housed at the University of Alberta Animal Holding Unit. All experimental protocols were approved by the Animals Ethics Committee of the University of Alberta. The rats were divided randomly into five groups of 3 animals each and the pharmacodynamic response was assessed following subcutaneous administration of the sCT or analogue equivalent to 20 IU sCT/kg body weight. Rats were anesthetized using Isoflurane inhalation anesthesia and the 200 µl blood samples were obtained in heparinized Eppendorf microtubes before drug injection. Then 100 µl of sCT or equivalent dose in 20 mM Sodium Acetate buffer pH 5 was sub cu injected and the blood samples were collected 1, 2, 3 and 4 hrs post injection from jugular vein. Blood plasma was obtained by centrifuging the samples at 5000 rpm for 10 min and collecting the supernatant. Plasma calcium level was assayed by QuantiChrom™ Calcium Assay Kit (BioAssay Systems, CA USA) and the plasma phosphate level was assayed by QuantiChrom™ Phosphate Assay Kit (BioAssay Systems, CA USA).

Figure 6:
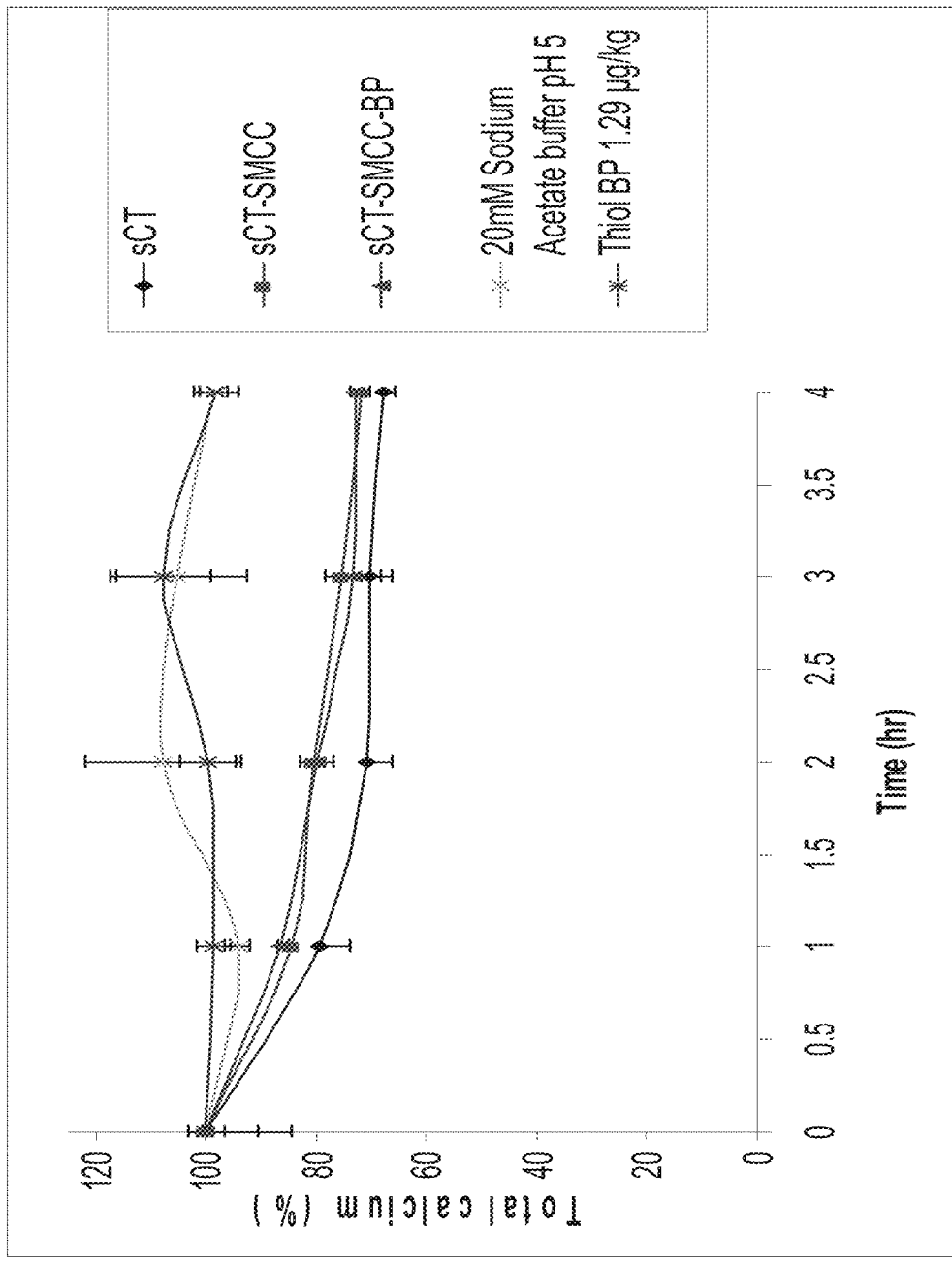
FIG. 6 shows the effect of sCT analogue on plasma calcium levels in normal rats. Rats were sub cu injected with 20 IU/kg sCT or equivalent. Blood was collected at 0, 1, 2, 3 and 4 hrs intervals and the amount of calcium in plasma was analyzed.

The biological effect of subcutaneously administered sCT, sCT-SMCC and sCT-BP in terms of their effect on plasma calcium level in normal rats are shown in FIG. 6 (a). At sCT equivalent doses, percentage of plasma calcium reduction induced by sCT, sCT-SMCC and sCT-BP were similar with values of 20.33±5.5%, 15.27±2.35% and 13.45±1.64% respectively at first hour. Similarly, in second hour post administration sCT reduced plasma calcium by 28.98±4.65%, sCT-SMCC by 19.43±2.32% and sCT-BP by 12.47±5.09%. At third hour post administration calcium level was reduced by 29.85±4.11, 24.48±2.83 and 26.62±5.28, respectively by sCT, sCT-SMCC and sCT-BP. At the end of the experiment by 4 hour post dosing the total percentage calcium reduction induced by sCT, sCT-SMCC and sCT-BP were 32.03±2.11%, 28.05±2.08% and 27.36±2.28% respectively. All values were compared to the 20 mM Acetate buffer pH 5 treated controls over the same period. Similarly, the calcium lowering effect of sCT-BP was confirmed to be due to sCT by dosing an equivalent amount of thiol-BP alone in the same buffer.

Figure 7:
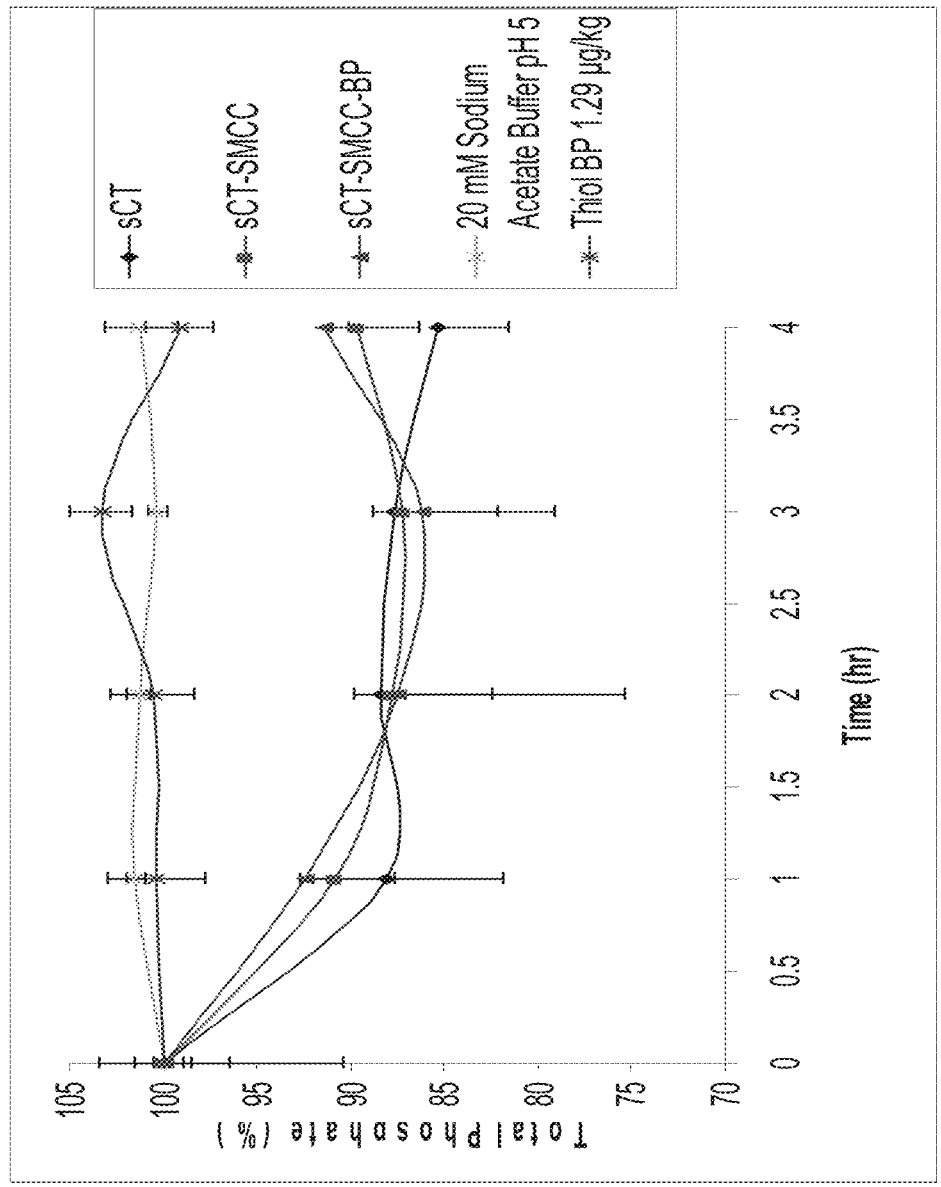
FIG. 7 shows the effect of sCT analogue on plasma phosphate levels in normal rats. Rats were sub cu injected with 20 IU/kg sCT or equivalent. Blood was collected at 0, 1, 2, 3 and 4 hrs intervals and the amount of phosphate in plasma was analyzed.

The effect of subcutaneously administered sCT, sCT-SMCC and sCT-BP in terms of their effect on plasma phosphate level in normal rats (FIG. 7) was also investigated. At the beginning sCT had highest impact on phosphate level reduction. Total percentage of phosphate reduction induced by sCT, sCT-SMCC and sCT-BP were 11.91±6.24%, 9.18±1.87% and 7.65±4.73% respectively at first hour. In the second hour after administration, sCT reduced plasma phosphate by 11.64±13.01%, sCT-SMCC by 12.18±2.03% and sCT-SMCC-BP by 12.47±5.09%. However, at the end of the experiment by 4 hour post dosing the total percentage phosphate level started to increase and the final decrease induced by sCT, sCT-SMCC and sCT-SMCC-BP were 14.69±3.71%, 10.4±0.54% and 8.54±5.11% respectively. All values were compared to the 20 mM Acetate buffer pH 5 treated controls over the same period. Similarly, the phosphate lowering effect of sCT-BP was confirmed to be due to sCT by dosing equivalent amount of thiol-BP alone in the same buffer.

II. Synthesis and Evaluation of a Bioactive, Bone-Targeting PEGylated Salmon Calcitonin Analogue Materials Salmon calcitonin was purchased from Calbiochem, USA and the NHS-PEG-MAL was from Creative Biochem, USA. Thiol functionalized Bisphosphonate (Thiol-BP) was purchased from Surfactis Technologies Inc, France. HPLC grade water, Dimethyl Sulfoxide (DMSO) and other reagents were from Sigma-Aldrich (Saint Louis, Mo., USA).

Methods and Results

Synthesis of Thiol Reactive sCT Analogue and Reaction Condition Optimization

In a pilot study, sCT in DMSO (13.72 mg/ml) was mixed with NHS-PEG-MAL in DMSO (51 mg/ml) in 1:5 molar ratio and the reaction between the primary —$NH_2$ in sCT and NHS group of NHS-PEG-MAL was allowed to proceed at room temperature with constant stirring for 60 minutes. Then the effect of NHS-PEG-MAL concentration was studied using sCT:NHS-PEG-MAL at 1:1, 1:2, 1:3, 1:5 and 1:7 mol/mol ratios in the above manner for 60 minutes. Similarly, the effect of reaction time was also studied by carrying the above reaction for 15, 30, 45 and 60 minutes using 1:3 molar ratio of sCT:NHS-PEG-MAL. In all cases, the reaction products were monitored by MALDI-TOF and the complete loss of sCT peak was considered as the parameter for the completion of reactions.

Figure 8:
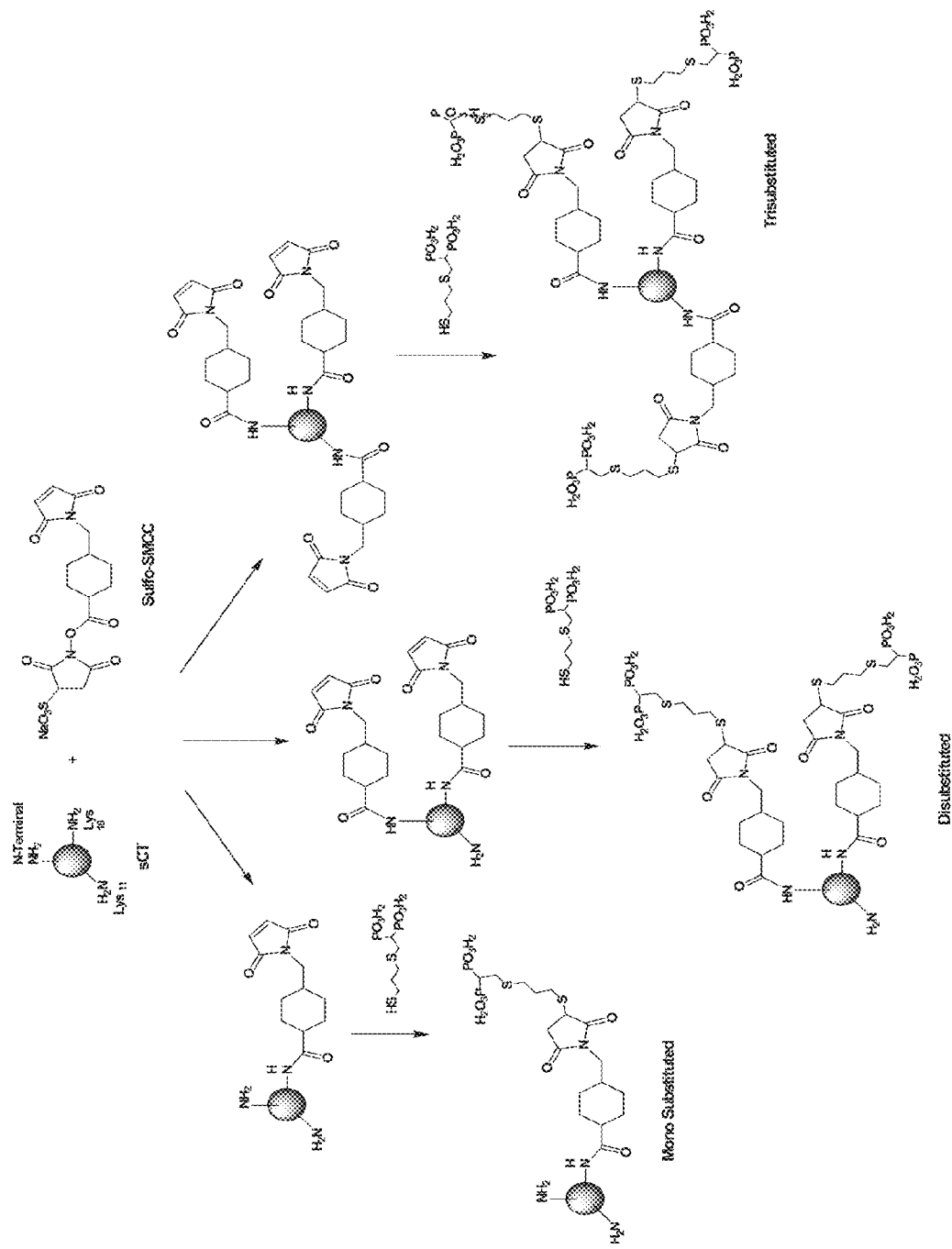
FIG. 8 shows the probable products when sCT is reacted with NHS-PEG-MAL followed by the reaction of sCT-PEG-MAL intermediate with thiol BP.

Possible reaction products of sCT with NHS-PEG-MAL are shown in FIG. 8. sCT has three primary amines at Lys 11, Lys 18 and N-terminal, which can react with the NHS functional group of NHS-PEG-MAL to generate three intermediate conjugates: mono-, di- and tri-substituted thiol reactive sCT analogues. The MALDI-TOF spectra of sCT showed a peak at 3433.7. The peak intensity and area in MALDI-TOF analysis showed that the formation of di-substituted favored over mono-substituted. Loss of sCT peak and major peaks representation NHS-PEG-MAL suggested that the reaction was complete. DMSO was chosen as the reaction medium because of the instability of NHS and sCT in aqueous solutions.

Coupling Free Thiol Containing BP with Functionalized Thiol Reactive sCT Analogue and Reaction Condition Optimization Before proceeding with the reaction, the amount of available reactive free thiol groups present in Thiol-BP was calculated by Ellman's thiol assay. Briefly, 50 µl of 4 mg/ml Ellman's Reagent Solution in 0.1 M sodium phosphate, pH 8.0, containing 1 mM EDTA was added to 250 µl of Thiol-BP solution, mixed and incubated at room temperature for 15 minutes. The yellow color developed was then measured at 412 nm using microplate reader. The amount of free thiol group was obtained using a calibration curve obtained with L-Cysteine as a control. Accordingly, the amount of thiol BP used was calculated based on these assays.

Functionalized thiol reactive sCT analogue were added intermittently with constant stirring to Thiol-BP solution in 100 mM Sodium Acetate buffer pH 6.8 at 1:20 molar ratio and the reaction between the thiol reactive MAL groups in functionalized sCT and SH group of Thiol-BP was allowed to proceed at room temperature in dark with constant stirring for 2 hours. The effect of buffer on the coupling to MAL and SH was studied using 100 mM Ammonium Acetate pH 6.8 and 100 mM Sodium Phosphate pH 6.8 buffers as above. Similarly, the effect of buffer concentration on this reaction was studied using 10, 50 and 100 mM Sodium Phosphate pH 6.8 in the above manner. Finally the effect of Thiol-BP concentration was determined by carrying the above reaction in 100 mM Sodium Phosphate pH 6.8 using functionalized sCT: Thiol-BP at 1:5, 1:10, 1:20 and 1:40 molar ratios as above.

In all cases, the reaction products were monitored by MALDI-TOF and the peak properties of reaction products were considered as the parameter for process optimization. Finally, the unreacted BP was removed by dialysis (MWCO 2000 D, Spectrum Laboratory, USA) against 20 mM Sodium Acetate buffer pH 5 (3× every 3 hours, 5× every 12 hours).

Determination of the Extent of BP Coupling Per sCT

Amount of sCT in sCT analogue was determined by Micro BCA protein assay. Briefly, an aliquot of 100 μl suitably diluted sample was mixed with 100 μl of working reagent (micro BCA reagent A, B and C in a volume ratio of 50:48:2). The mixture was incubated at 37° C. for 2 h and then cooled down to room temperature. Absorbance at 562 nm was measured using 96-well microplate reader. The amount of sCT was calculated by converting the absorbance into mass using the standard curve.

Similarly, the amount BP present in the same amount of sCT-PEG-BP was determined in terms of total phosphate present using an organic phosphate assay. Briefly, 50 μl of suitably diluted samples was mixed with 30 μl of 10% $Mg(NO_3)_2$ in 95% ethanol in glass tubes and ashed over a flame. After boiling in 0.3 mL of 0.5 N HCl for 15 min, 0.1 mL of ascorbic acid (10% w/v) and 0.6 mL of $(NH_4)_6Mo_7O_{24}.4H_2O$ (0.42% w/v in 1 N $H_2SO_4$) were added to the tubes and the samples were incubated at 37° C. for 1 h. The absorbance of the blue color developed were then determined at 820 nm. The amount of phosphate was calculated using the calibration curve obtained for Thiol-BP. The calibration curve for Thiol-BP was in turn obtained using the calibration curve obtained for Alendronate sodium as a standard.

The BP concentration in combination with the sCT concentration of a sample was used to calculate the number of BPs coupled per sCT. The BP concentration (μM) of a sample was divided by its sCT concentration (μM) to yield an average number of BP coupling per sCT.

Since sCT has three available —$NH_2$ groups as reaction sites for the NHS group in NHS-PEG-MAL, the effect of NHS-PEG-MAL concentration in the substitution was studied using sCT:NHS-PEG-MAL at 1:1, 1:2, 1:3, 1:5 and 1:7 mol/mol ratio. Reaction was incomplete for sCT:NHS-PEG-MAL at 1:1, 1:2 molar concentration as a peak at 3430 representing sCT was seen on MALDI-TOF. However, it was complete after the ratio of 1:3 mol/mol as shown by the loss of the sCT peak. At lower NHS-PEG-MAL concentration mono-substituted products were predominant. While di and tri-substitution favored with increasing NHS-PEG-MAL concentration. Tri-substituted products were not remarkable until 1:3 molar ratios, and were highly noticeable with further increment in NHS-PEG-MAL concentration. However, di-subsititted products were major products at 1:3 molar ratios. Since the formation of tri-substituted products was remarkably noticeable after 1:3 molar ratio and the reaction was incomplete before it, sCT:NHS-PEG-MAL at 1:3 mol/mol ratio was selected for further reactions. These results suggest that by monitoring NHS-PEG-MAL concentration PEG substitution on sCT can be relatively controlled.

Effect of reaction time was studied to optimize the duration of reaction. Reaction was incomplete before 30 minutes as a peak at 3430 representing sCT was seen on MALDI-TOF. However, it was complete at or after 30 minutes as shown by the loss of the sCT peak. Formation of di and tri-substituted products were increased with time. Prolonged reaction time allowed more time for PEG molecules which were in excess to collide with more primary amines in sCT to generate di- and tri-substituted compounds. Based on those results, a reaction time of ~45 min was chosen. However, there may be no harm in prolonged reaction time, except in the alteration of the BP substitution ratio.

The expected reaction products after conjugation of functionalized sCT with Thiol-BP are shown in FIG. 8. MALDI-TOF results of conjugates using 100 mM pH 6.8 Sodium Phosphate, Sodium Acetate and Ammonium Acetate buffers were obtained. Sodium Acetate was initially chosen as the suitable reaction media because in literature, this was reported to stabilize aqueous unstable sCT better than other buffers. However, the pH was adjusted to 6.8 as it was optimum for the reaction between MAL in functionalized sCT and SH in thiol-BP. Since the buffering capacity of any buffer is greatest at around its pKa which is 4.75 for Sodium acetate buffer, at higher pH the reaction was unfavorable as the addition of sCT and Thiol-BP could alter the pH away from the optimal reaction pH that could not be efficiently resisted by the buffer. Although Ammonium acetate buffer was reported by the same authors to have relatively better sCT stabilizing effect, reaction was more favorable in 100 mM phosphate buffer pH 6.8 as shown by the appearance of tri-substituted products. This could be due to the higher buffer capacity of phosphate buffer at that pH irrespective of sCT stability issues. Unlike in phosphate buffer tri-substituted products were not seen in case of acetate buffers. Since the MAL and SH is completed before 2 hrs at room temperature, 100 mM phosphate buffer pH 6.8 was selected because of its reaction favoring effect. We assumed that the stability/solubility of sCT in phosphate buffer at the final concentration used in reaction was not a major issue as it was below 1 mg/ml and phosphate buffer was immediately exchanged by dialyzing with 20 mM Sodium Acetate buffer pH 5 with better sCT stabilization effect.

Since the coupling reaction was favorable phosphate buffer, the effect of buffer concentration in reaction was evaluated. This was partially based on the fact that pure CT was unstable and has tendency of aggregation and precipitation in concentrated buffers including phosphate buffer. 10, 50 and 100 mM phosphate buffers pH 6.8 were used in the reaction. As expected the reaction was favorable in more concentrated buffers. Mainly di-substituted products were evident in 10 mM buffer but all three products were seen in 50 and 100 mM with the formation of di-substituted products being more favorable. Uncharacterized peaks at about 18000 kD were seen in case of 10 mM but not with 50 and 100 mM. Form these findings the 100 mM phosphate buffer was selected for further reactions. Presence of PEG increased the solubility and stability of sCT in buffered solution. This was evidenced by the amount of sCT present in final sample after dialysis in subsequent experiments.

Finally, the effect of Thiol-BP in the reaction using functionalized sCT-PEG-MAL: Thiol-BP in 1:5, 1:10, 1:20 and 1:40 molar ratios was evaluated. However, the actual ratios of SH for available MAL would be 1:2.5, 1:5, 1:10 and 1:20 mol/mol if we consider the average of two PEG-MAL per sCT. Formation of di-substituted products was always higher and more favorable and the reaction was more favorable with an increment in Thiol-BP ratio. Formation of tri-substituted products also increased with increased BP ration. Presence of some low intensity uncharacterized peaks could be degradation products due to the effect of laser. From these results, a ratio of 1:20 was chosen for further reactions.

Tris-Tricine SDS Gel Electrophoresis sCT analogues were analyzed by Tris-Tricine sodium dodecyl sulfate polyacrylamide gel electrophoresis (SDS-PAGE) under non-reducing conditions. Briefly, 10 µL of sample solution was mixed with 20 µL of loading buffer, premixed protein sample buffer for peptides and small proteins (Bio-Rad, USA, Cat#161-0739) and loaded in wells of the 16.5% Tris-Tricine/Peptide precast gel (Bio-Rad, USA, Cat#161-1107). Reference Polypeptide SDS-PAGE Standards (Bio-Rad, USA, Cat#161-0326) was diluted with sample buffer at 1:20 v/v ratio, heated at 95° C. for 5 minutes, cooled and loaded at 5 µl/well. After electrophoresis at 100 V using Tris/Tricine/SDS buffer (Biorad, Cat#161-0744), the gel was fixed with a solution of 40% methanol, 50% water and 10% acetic acid for 30 minutes. Fixing solution was then removed and the gel was stained for 1 hr with Coomassie brilliant blue R-250 (0.008% in 10% acetic acid) at 95° C. for 20 seconds, followed by staining at room temperature for 15 minutes. Gels were de-stained in water overnight, scanned and saved as an image.

sCT had and average of 2.17 BPs per molecules. This is in accordance with the previous results of the more favorable di-substitution reaction relative to mono and tri-substitution. As the number of BP substitution increases so does the bone mineral binding affinity of BP conjugated protein, higher substitution would still be desirable as long as it does not severely harm sCT secondary structure, and receptor binding affinity.

Results of Tris-tricine SDS-PAGE are shown in FIG. 9. Lane 1 represents molecular weight markers, 2 is for sCT, 3 for sCT-PEG-BP and 4 for sCT-PEG. Single band for sCT appeared at about 3.49 kD and two bands were seen in case of sCT-PEG above 6.5 kD and below 14.4 kD. Similarly sCT-PEG-BP appeared as two bands above the position of sCT-PEG. All three substitution products as shown in MALDI-TOF were not seen in SDS-PAGE. From the gel scan it appears that the mono substituted products was not present. However, in MALDI the peak ratio of mono substituted products were always noticeably higher than tri-substituted products. Thus it can be assumed that the appeared products were major mono and di-substituted products although they were seen in an altered position than standard molecular weight markers. The presence of PEG has interference effect on the analysis.

Determination of Bone Targeting Potential, and Bone Mineral Affinity and Specificity Bone targeting potential of sCT analogue was evaluated by determining the effect of sCT modification (due to chemical coupling) upon its bone mineral affinity. Specific volume of purified sCT analogue solution containing 10 µg of sCT was mixed with 1 mg Hydroxyapatite (HA) in 150 µL 100 mM phosphate buffer (pH 7.0) in microcentrifuge tubes in duplicate to give a final concentration of 66.67 µg/ml sCT. As a reference, control samples were incubated in tubes without HA (i.e., 0% of binding).

The tubes were incubated at room temperature on a shaker for 1 h, and centrifuged at 5000 g for 5 minutes to separate the HA from the supernatant. sCT concentration in the supernatant was determined using the BCA microprotein assay (Pierce, USA) as described above. HA centrifugate remaining after removal of supernatant was washed five times using 1 mL buffer each time and the last washing after centrifugation at 5000 g for 5 minutes was collected. Both the washings and the HA centrifugate were then analyzed for sCT as described above. The amount of sCT in the supernatant, washings and HA centrifugate was then inferred by measuring the absorbance at 562 nm, with a value of 100% for control samples without HA.

Bone mineral specificity of sCT analogue was then determined in the above manner using HA, calcium carbonate, calcium pyrophosphate, tricalcium phosphate and calcium oxalate.

Figure 10A:
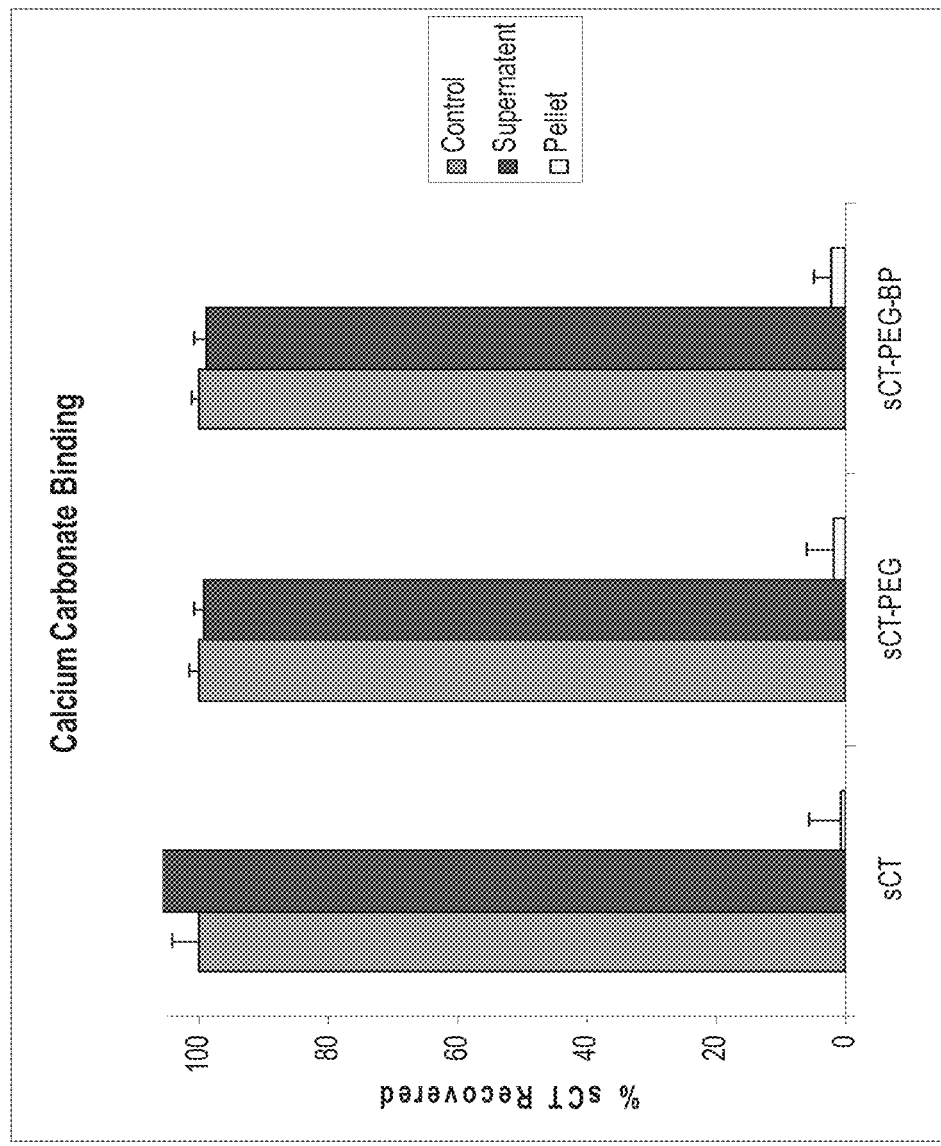
FIG. 10 shows the calcium carbonate (a), Calcium oxalate (b), Calcium pyrophosphate (c) and Tri-calcium phosphate (d) binding assay of conjugates to determine their bone mineral specificity and Hydroxyapatite (HA) binding assay (e) of conjugates to determine their bone mineral affinity. sCT or equivalent sCT-PEG and sCT-PEG-BP was incubated for 1 hour with calcium salts in 100 mM pH 7 phosphate buffer and the amount of sCT in supernatant and centrifuged pellet was determined by micro-BCA protein assay.
Figure 10B:
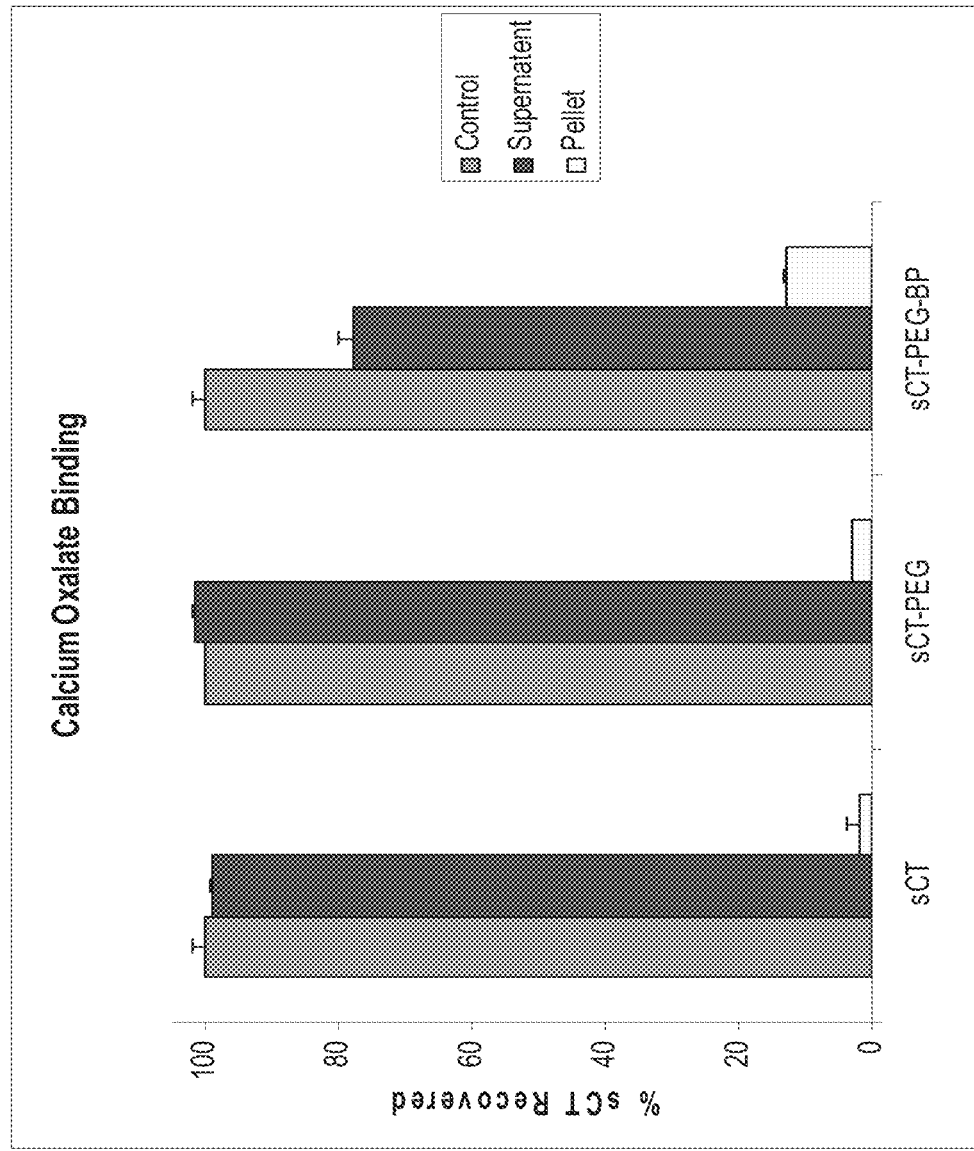
Figure 10C:
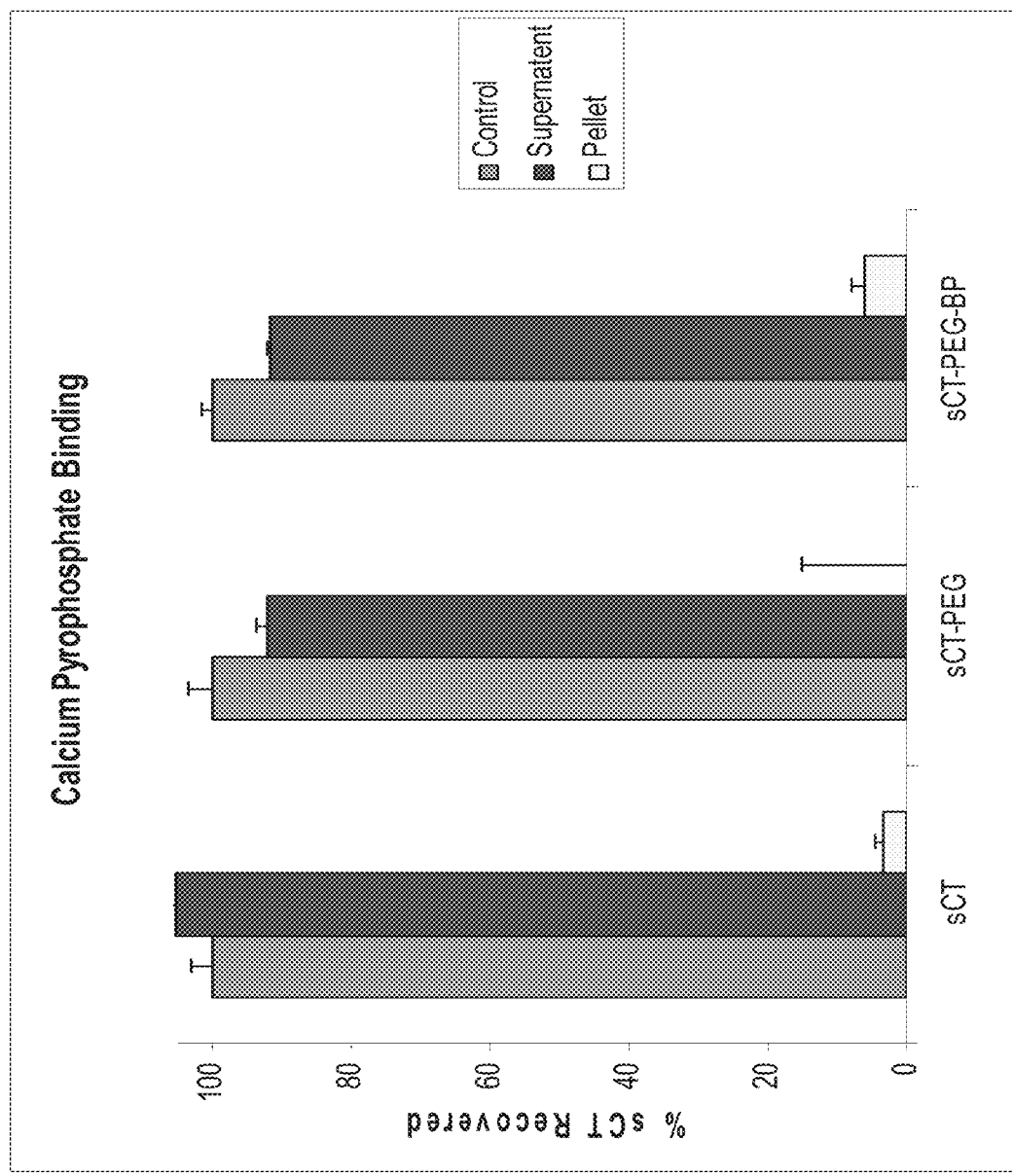
Figure 10D:
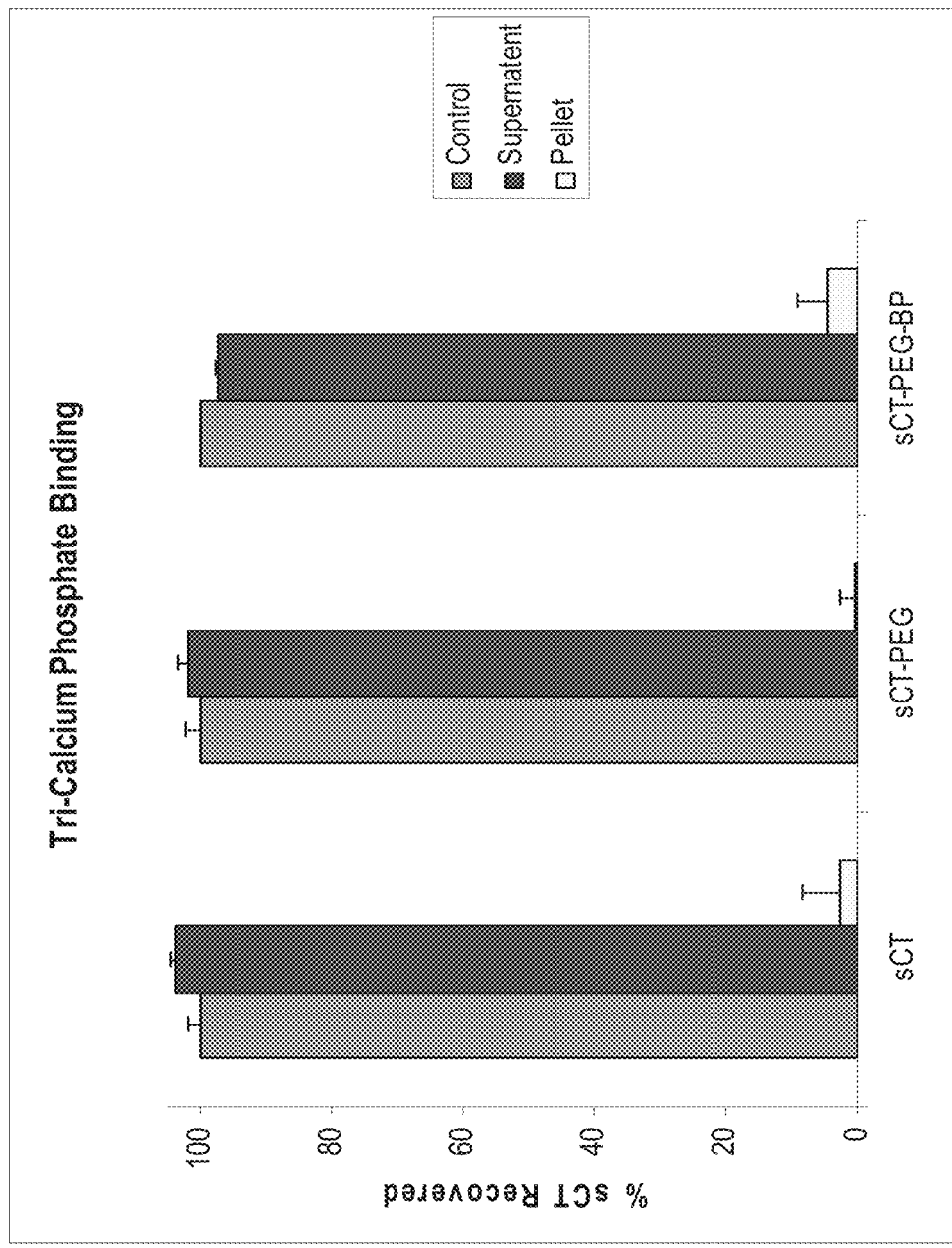
Figure 10E:
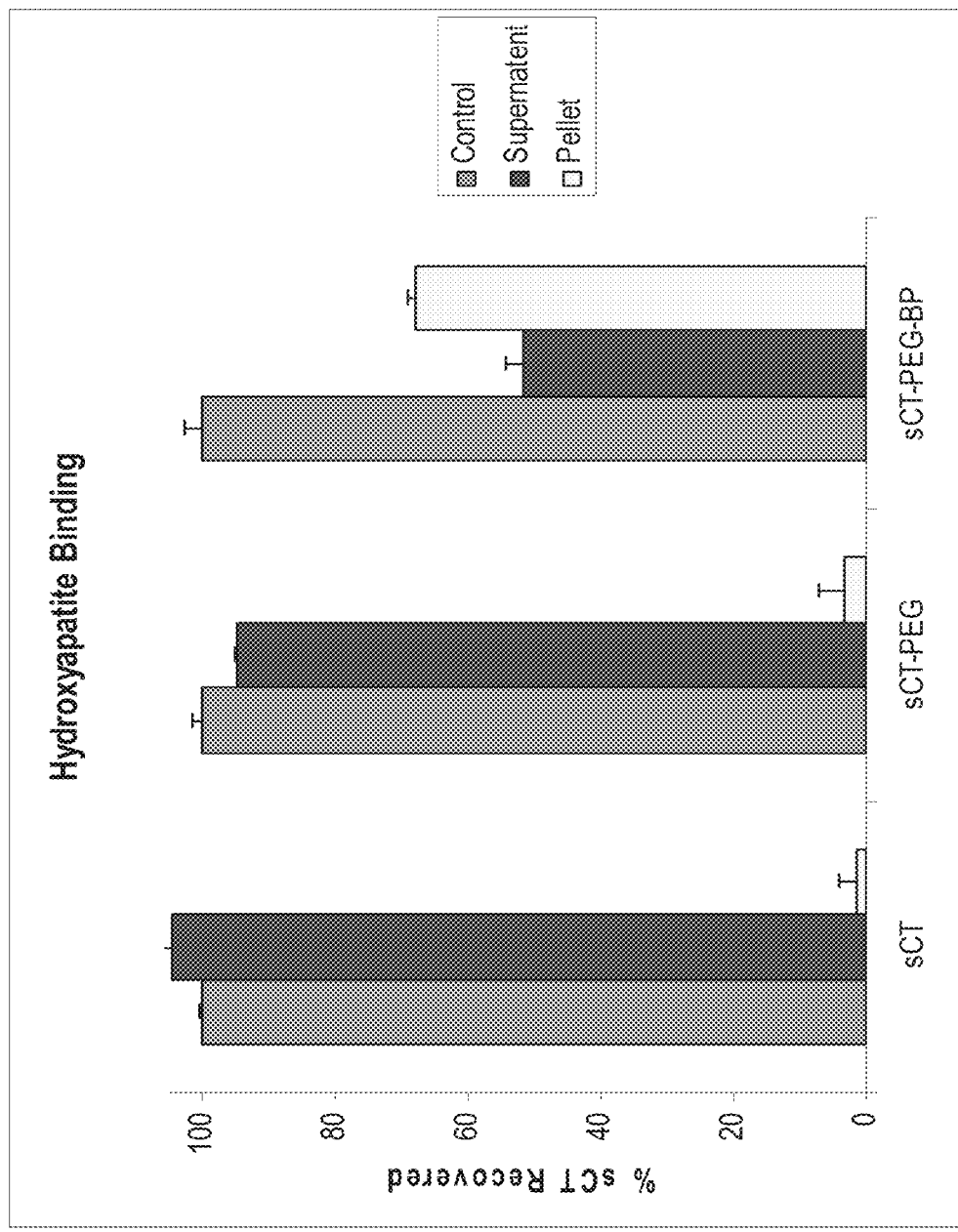

When all compounds were assayed directly (i.e., without any calcium salts or HA), the absorbance of protein in those samples was readily detected in the supernatant. This concentration was taken as 100% recovery for the further calculations. Incubation of sCT or sCT analogues with equivalent amount of sCT with Calcium carbonate (10a) did not significantly reduce the sCT concentration in the supernatant solution. This was further confirmed by the sCT assay of the Calcium Carbonate pellet obtained after repeated washing and centrifugation. In each case the sCT concentration of the last washing solution of pellet was also assayed for sCT and we did not detect any sCT in there (data not shown). About 85% of sCT was recovered in supernatant and 15% from pellet when sCT-PEG-BP was incubated with Calcium oxalate (FIG. 10b). However it did not significantly reduce the sCT concentration in the supernatant solution in case of sCT and sCT-PEG. Similarly, About 90% of sCT was recovered in supernatant and 10% from pellet when sCT-PEG or sCT-PEG-BP was incubated with Calcium Pyrohosphate (FIG. 10c). However it did not significantly reduce the sCT concentration in the supernatant solution in case of sCT. Likewise, no significant difference in the affinity of sCT or sCT-PEG were seen in incubation with Tri-Calcium Phosphate. But, about 5% sCT was bound in case of sCT-PEG-BP (FIG. 10d). However, in HA binding assay about 65% was bound in HA and the remaining in supernatant (FIG. 10e) in case of sCT-PEG-BP. substantially reduced the sCT concentration in the supernatant was due to its BP-mediated binding to the HA. But, sCT and sCT-PEG did not significantly bind to HA. The alteration of primary amines in sCT alone (by the cross-linker PEG conjugation chemistry) did not improve HA binding, as represented by the lack of sCT-PEG control conjugate HA binding. After centrifugation and complete removal of unbound sCT, the majority of remaining sCT was detected in the pelleted HA centrifugate compared to other calcium salts. As HA is the principal mineral found in bone matrix, the in vivo administration of sCT-PEG-BP conjugates should lead to improved bone accumulation of sCT compared to free sCT or sCT conjugates without BP.

Determination of Secondary Structure of sCT Analogue by Circular Dichroism

For a more detailed analysis of the influence of structural alteration of sCT on secondary structure of sCT analogue, the circular dichroism (CD) spectrum of sCT, sCT-PEG and sCT-PEG-BP was measured in the 20 mM acetate buffer pH 5.0. CD spectra were obtained with a ConvCD spectrophotometer instrument. Spectra were acquired over a wavelength range of 190 to 260 nm. The N2 flow rate was set at 5 l/min. The sample cuvette (100 μL) was cleaned with 20 mM Sodium Acetate buffer pH 5, and the spectra of test samples, which comprised of ~400 μg/mL of sCT or equivalent the same buffer, were recorded with the corresponding buffer serving as blanks.

Figure 11:
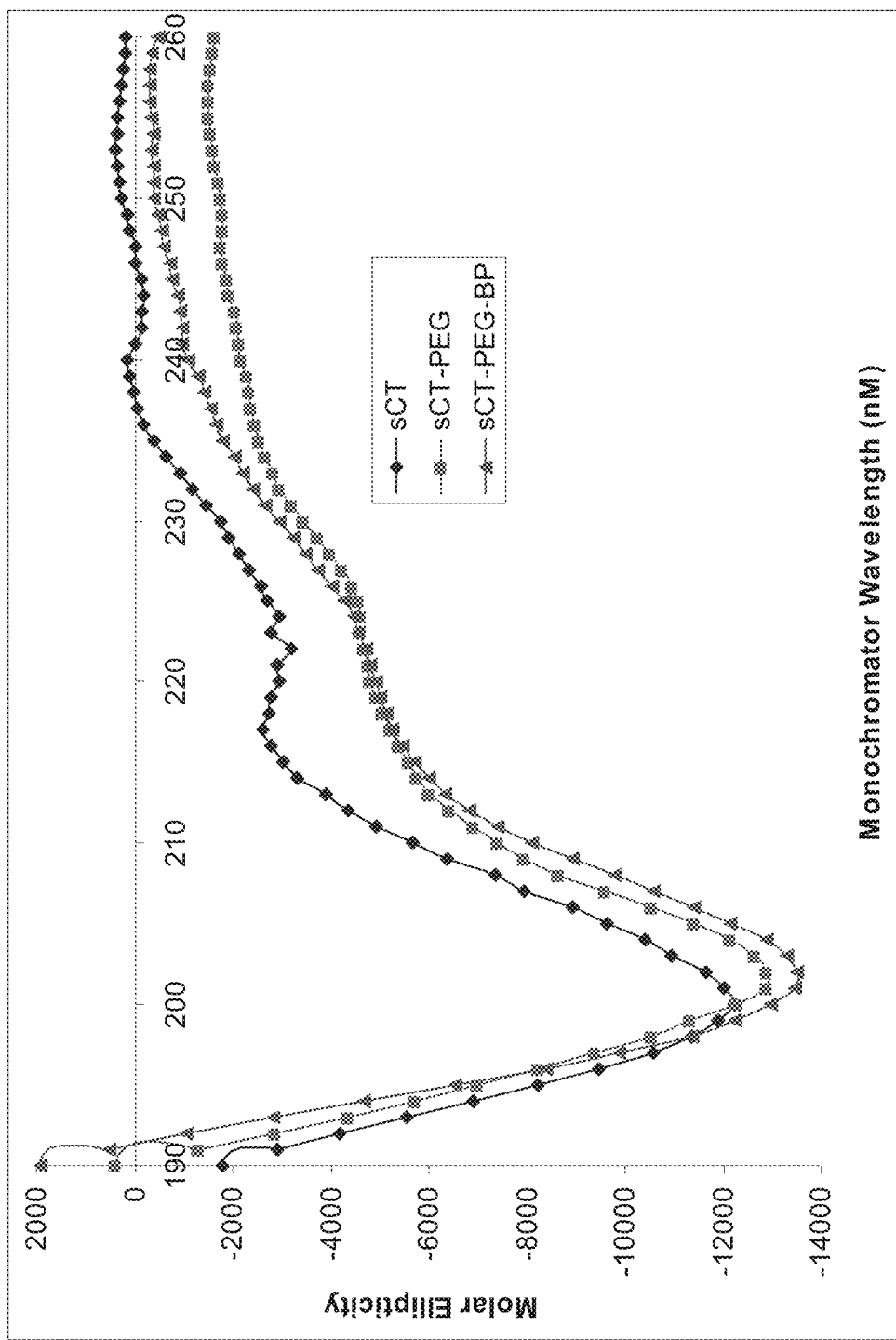
FIG. 11 shows the circular dichroism spectra of sCT, sCT-PEG and sCT-PEG-BP to determine the effect of PEG or PEG-BP conjugation on sCT secondary structure.

As it can be observed from FIG. 11, circular dichroism (CD) spectrum sCT shows a minimum at around 200 nm, indicating that the peptide assumed a random coil conformation. sCT has very little helical content as demonstrated by the low magnitude of the ellipticity at 222 nm. The shape of the CD curve of sCT-PEG and sCT-PEG-BP retained the peak at 222 nm and the peak at 200 shifted towards higher nm. In addition a positive peak appeared at below 200 nm in sCT-PEG or sCT-PEG-BP, This indicates the tendency of PEG to shift sCT secondary structure toward relatively more stable and less aggregation prone helical structure. CD results show that in the same solvent, sCT-PEG and sCT-PEG-BP displayed a relatively stronger α-helical character as shown by negative band at 222 nm, a positive band at 194 nm, and shifting of band at 202 nm towards 205 nm compared to sCT. Although a perfect helical structure was not seen in case of pegylated sCT analogues, this still could have a significant impact towards sCT solution stability. As shown in later experiments, pegylation had no adverse effect in receptor binding and bioactivity of sCT. In context of unaltered activity, shifting of sCT structure toward helical shape is desirable.

Cytotoxycity of sCT Analogue on Osteoclast Precursor Bone Marrow RAW 264.7 Cells RAW 264.7 cells (ATCC VA, USA) were seeded on 96 well plates at an initial density of $2 \times 10^4$ cells/well and incubated in 200 μl GIBCO High Glucose 1× Dulbecco's Modified Eagle Medium (DMEM) (Invitrogen CA, USA) supplemented with 4.5 g/L D-Glucose, L-Glutamine, 110 mg/L Sodium Pyruvate, 10% heat inactivated fetal bovine serum (FBS) and 1% Penicillin-Streptomycin (10000 U/mL; Invitrogen) in a Thermo Fisher Scientific Water Jacketed $CO_2$ incubator (37° C., 5% $CO_2$) until the cells were 80% confluent.

After 72 hrs, media was replaced by 200 μl basic DMEM media without FBS and incubated for 30 minutes. Then the media was replaced by 100 μl basic DMEM media containing sCT, sCT-PEG and sCT-PEG-BP equivalent to 100, 500 and 1000 nM final sCT concentration and the cells were incubated for 4 hrs at 37° C. sCT containing media was then replaced by 100 μl basic media containing (3-[4,5-dimethylthiazol-2-yl]-2,5-diphenyl tetrazolium bromide) (MTT) at a concentration of 100 μg/well and incubated for another 4 hrs at 37° C. After removing the supernatant and washing twice with phosphate buffer saline, purple formazan crystals formed were dissolved in 200 μl solubilization solution (in vitro toxicology assay kit, # TOX-1, Sigma Aldrich, St. Louis, USA) and the absorbance was measured at 570 nm using microplate reader. Experiment was performed for n=8 and the absorbance of wells containing cells without sCT treatment was considered as 100% viable and used to calculate the relative viability of sCT treated cells.

Figure 12:
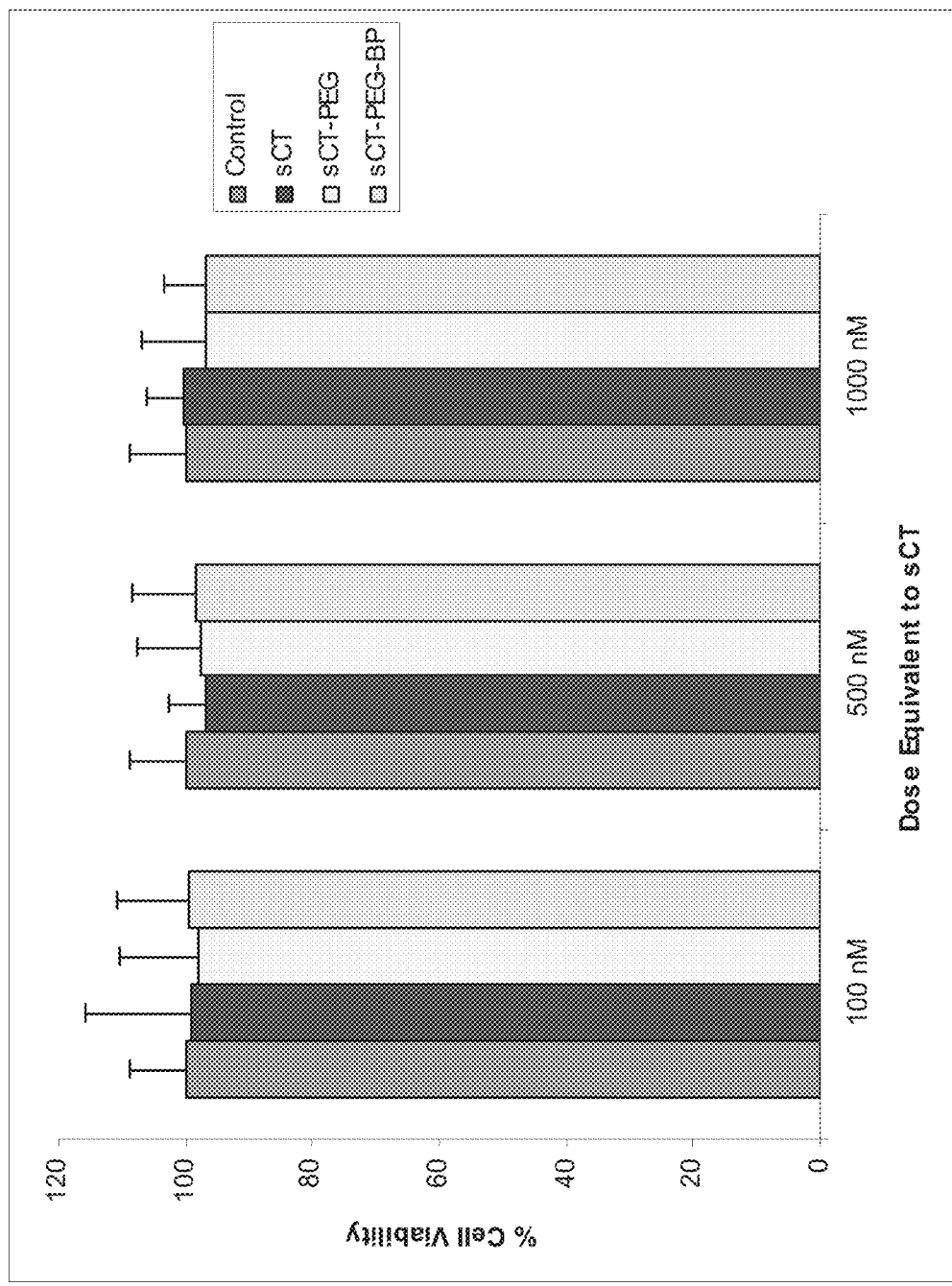
FIG. 12 shows the in vitro cytotoxycity of sCT analogue on osteoclast precursor bone marrow RAW 264.7 cells determined by MTT assay. 20000 Raw cell/well in 96 well plate (n=8), cultured for 3 days and treated with sCT or equivalent followed by incubation at 37° C. for 4 hours in basic DMEM media. Cells were treated by 100 µg/well MTT in basic DMEM media and the absorbance of formazan crystal solution was measured spectrometrically at 570 nm.

Cytotoxicity of sCT analogue was assessed on human osteoclast precursor bone marrow RAW 264.7 cells. sCT and sCT analogues showed low levels of cytotoxicity as measured by the absorbance of formazan solution formed after 4 hours incubation with compounds, compared to that seen with untreated media (FIG. 12). In all in vitro and in vivo bioactivity assay the maximum concentration used was equivalent to 100 nM sCT. However, cytotoxicity was determined for the concentration up to 1000 nM sCT or equivalent. Even at the highest concentration tested there was no significant difference in the viability of these cells. In MTT assay, mitochondrial dehydrogenases of viable cells cleave the tetrazolium ring of MTT yielding purple formazan crystals which are insoluble in aqueous solutions. Theys were dissolved in acidified isopropanol and the resulting purple solution was measured spectrophotometrically. An increase or decrease in cell number results in a concomitant change in the amount of formazan formed, indicating the degree of cytotoxicity caused by the test material.

Determination of Anti-Calcitonin Antibody Epitope Binding Specificity of sCT Analogue by ELISA sCT or sCT analogues equivalent to 1 μg/well were added in Calcium Phosphate coated Osteoclast Activity Assay Substrate plate (OCT USA, Inc.) in duplicate and the binding of BP to the calcium phosphate was allowed for 1 hours in the presence of 100 μl 100 mM Sodium Phosphate buffer pH 7. Plates were then washed three times with the same buffer containing 0.05% v/v Tween 80 (PBST). To avoid nonspecific binding, the wells were incubated with 3% w/v Bovine Serum Albumin for 1 h at room temperature. After washings, the wells were incubated with 1000 of 1:5000 diluted rabbit anti-salmon calcitonin primary monoclonal antibodies (US Biologicals, USA) for 1 h at room temperature. The wells were then washed three times with PBST and the bound antibodies were detected using secondary antibody, 1:5000 diluted goat anti-rabbit IgG conjugated with horseradish peroxidase (GAM-HRPO) for 1 h at room temperature. After final washings, 100 μl of 3,3',5,5'-tetramethylbenzidine (TMB substrate) was added to each well and incubated for 15 min at room temperature. The optical density (OD) was measured at 650 nm using an ELISA Vmax kinetic microplate reader (Molecular Devices Corp., California, and USA).

Figure 13:
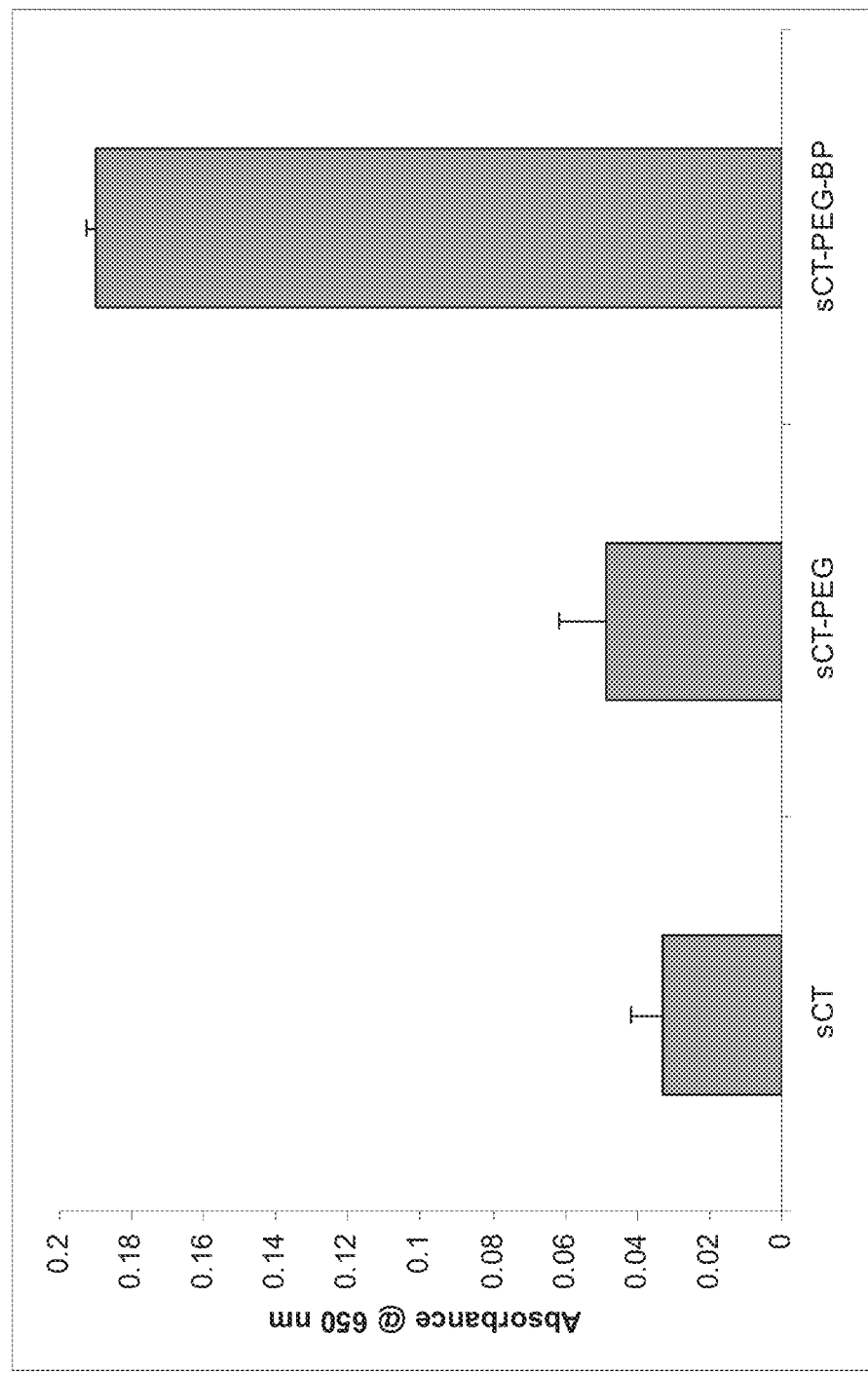
FIG. 13 shows the determination of anti-calcitonin antibody epitope binding specificity of sCT analogue by ELISA. Osteologic plate coated with calcium phosphate was incubated with sCT or equivalent (1 µg) in 100 µl 100 mM Phosphate buffer pH 7 for 1 hr, washed, blocked by BSA. Plates were then incubated with rabbit anti-sCT antibody followed by goat anti-rabbit IgG. TMB substrate was added and the absorbance of the developed color was measured at 650 nm.

FIG. 13 represents the result of anti-calcitonin antibody epitope binding specificity of sCT analogue by ELISA. sCT in conjugates bound to calcium phosphate in osteologic plates, binds to its specific rabbit anti-salmon calcitonin antibody. Which was then detected using HRPO conjugated goat anti-rabbit IgG as a secondary antibody and TMB substrate. The absorbance of sCT-PEG-BP was 5 times higher than that of native sCT and sCT-PEG, suggesting the affinity of conjugates for the bone surface and unaltered antibody epitope binding potential of sCT in them. However, absence of bone binding BP in sCT or sCT-PEG did not allow them to bind in plates as were not significantly detected in subsequent ELISA. As the systemically administered sCT is 40% serum albumin bound in circulation, the small absorbance in sCT or sCT-PEG could be explained by their non specific binding with bovine serum albumin used as a blocking agent.

Calcitonin Receptor Binding Affinity and In Vitro Bioactivity of sCT-Analogue

T47D cells were cultured in triplicate in RPMI-1640 culture medium containing 1% penicillin-streptomycin, 10% fetal bovine serum, and insulin (0.2 IU/mL). Cells were seeded on 48 well plates at an initial density of $5 \times 10^4$ cells/well and incubated in 95% air and 5% $CO_2$ at 37° C. for 2 days. Cells were then washed with HBSS and pre-incubated in RPMI-1640 culture medium devoid of FBS, insulin and antibiotics. Cells were then dosed with phosphodiesterase inhibitor, 3-isobutyl-1-methyl-xanthine (IBMX, 1 mM) and incubated at 37° C. for 30 min. 0, 10, 50 and 100 nM of sCT or equivalent sCT analogues were then added to the cells and incubated for 20 min at 37° C.

After removing the supernatant, cells were washed three times in cold phosphate buffer saline and resuspended in 500 µl of Cell Lysis Buffer. Cells were frozen at −20° C. and thawed with gentle mixing. The freeze/thaw cycle was repeated three times and the mixture was centrifuged at 600 g for 10 minutes at 2-8° C. to remove cellular debris. The supernatant was collected and stored at −20° C. cAMP concentrations were then measured using the cAMP Enzyme Immuno-Assay (EIA) kit (KGE002B, R & D systems, USA). Increased cAMP production in response to the different forms of sCT was calculated using a calibration curve constructed using standard cAMP. Values of cAMP concentration for native sCT was considered 100% for respective dosing and % change in cAMP concentration by equivalent sCT analogue relative to that of unmodified sCT was calculated.

Figure 14A:
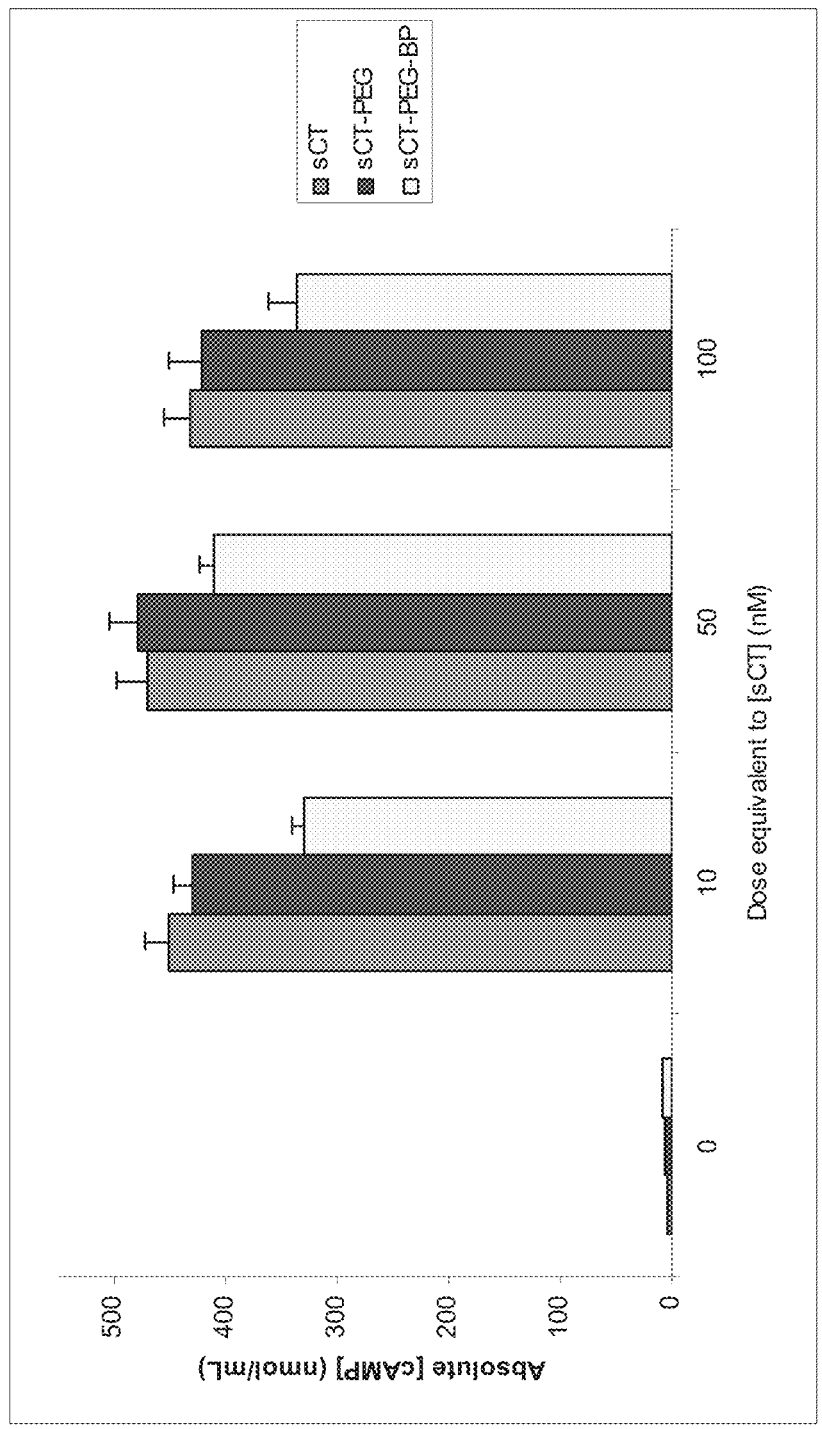
FIG. 14 shows the calcitonin receptor binding affinity and in vitro bioactivity sCT-analogue determined using intracellular cAMP stimulation in human T47D cells. 100000 cells/well were cultured for 2 days in 48 well plates in RPMI 1640 containing insulin and the Phosphodiesterase activity was blocked using 3-IBMX. Cells were then was treated with 0, 10, 50 and 100 nM sCT or equivalent and the generated cAMP was assayed by cAMP ELISA. (a) Absolute amount of cAMP (nmole/ml) and (b) cAMP (% maximal) as determined by considering the amount of cAMP generated by sCT for a particular concentration as 100%.
Figure 14B:
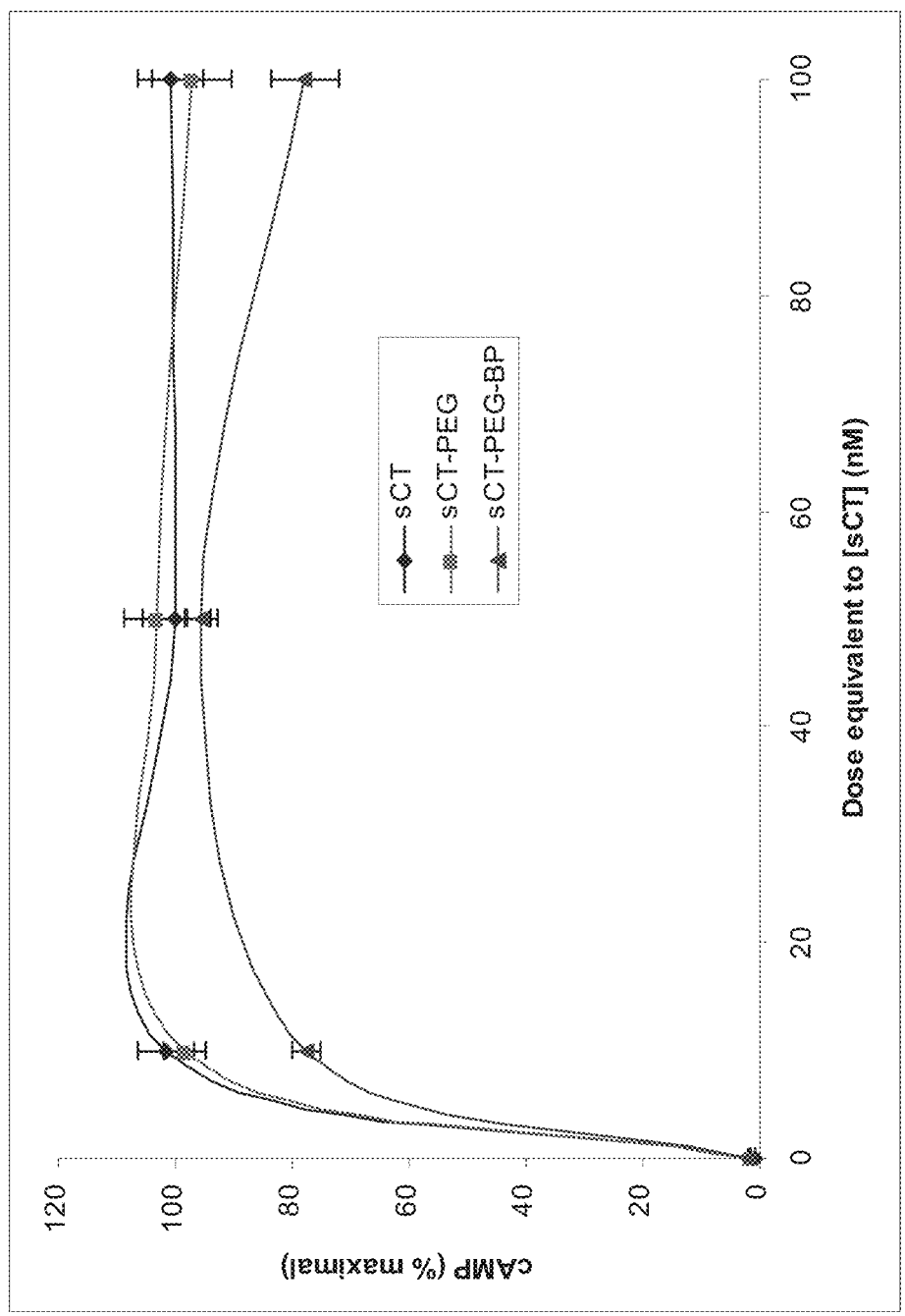

The ability for native sCT, sCT-PEG, and sCT-PEG-BP to bind to CTR to generate intracellular cAMP in the presence of a phosphodiesterase inhibitor is shown in FIG. 14. The absolute amount of cAMP generated is shown in FIG. 14(a) and the intracellular cAMP generating activities of sCT analogues compared to sCT is on FIG. 14(b). There was no significance difference in the cAMP generating abilities between sCT and sCT-PEG for all dose used. However, such activity was reduced by 20% in case of sCT-PEG-BP compared to native sCT. Since the antiresorptive effects of calcitonin are mediated by calcitonin receptor found primarily in bone-resorbing osteoclast cells (OC), 80% retention of sCT activity can be significant in these bone targeting analogues as they have the potential to be deposited in bone after their systemic administration. In case of untargeted forms their preferential accumulation was in kidneys, liver, lungs, spleen, heart and thyroid. In addition, increased circulation time by pegylation can also result higher metabolization of sCT and sCT-PEG compered to bone targeted forms. Similarly, in the context of competitive CT receptor uptake, the antiresorptive effect of bone targeted form could be significant.

In vivo Bioactivity Assay: Effect of sCT Analogue on Plasma Calcium and Phosphate Levels in Normal Rats Pharmacodynamic response of sCT analogue was evaluated by analyzing plasma calcium concentration in the rat model. Sprague Dawley female rats weighing 230-260 g (about 6 weeks old) were purchased from Charles River, USA and housed at the University of Alberta Animal Holding Unit. All experimental protocols were approved by the Animals Ethics Committee of the University of Alberta. The rats were divided randomly into five groups of 3 animals each and the pharmacodynamic response was assessed following subcutaneous administration of the sCT or analogue equivalent to 20 IU sCT/kg body weight. Rats were anesthetized using Isoflurane inhalation anesthesia and the 200 µl blood samples were obtained in heparinized Eppendorf microtubes before drug injection. Then 100 µl of sCT or equivalent dose in 20 mM Sodium Acetate buffer pH 5 was injected and the blood samples were collected 1, 2, 3 and 4 hrs post injection from jugular vein. Blood plasma was obtained by centrifuging the samples at 5000 rpm for 10 min and collecting the supernatant. Plasma calcium level was assayed by QuantiChrom™ Calcium Assay Kit (BioAssay Systems, CA USA) and the plasma phosphate level was assayed by QuantiChrom™ Phosphate Assay Kit (BioAssay Systems, CA USA).

Figure 15A:
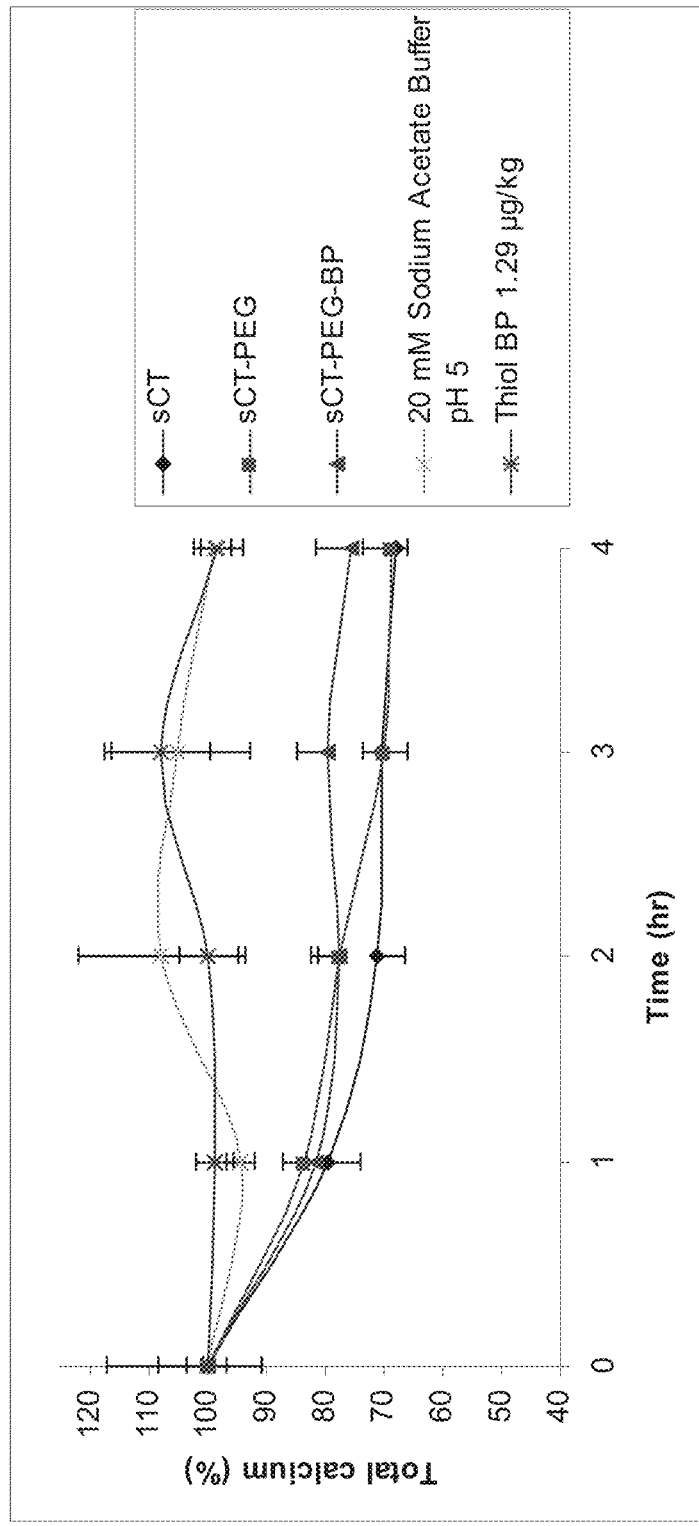
FIG. 15 shows the effect of sCT analogue on plasma calcium and phosphate levels in normal rats. Rats were subcutaneously injected with 20 IU/kg sCT or equivalent. Blood was collected at 0, 1, 2, 3 and 4 hrs intervals and the amount of calcium and phosphate in plasma was analyzed.

The biological effects of subcutaneously administered sCT, sCT-PEG and sCT-BP in terms of their effect on plasma calcium level in normal rats are shown in FIG. 15(a). At sCT equivalent doses of sCT, percentage of plasma calcium reduction induced by sCT, sCT-PEG and sCT-PEG-BP were similar with values of 20.4±5.5%, 17.6±3.6% and 19.7±1.9% respectively at first hour. Similarly, in the second hour after administration sCT reduced plasma calcium by 29.9±4.9%, sCT-PEG by 23.6±3.6% and sCT-PEG-BP by 23.6±4.9%. At the end of the experiment by 4 hour post dosing the total percentage calcium reduction induced by sCT, sCT-PEG and sCT-PEG-BP were 33.1±2.1%, 32.4±4.74% and 25.5±6.1% respectively. All values were compared to the 20 mM Acetate buffer pH 5 treated controls over the same period. Similarly, the calcium lowering effect of sCT-PEG-BP was confirmed to be due to sCT by dosing an equivalent amount of thiol-BP alone in the same buffer.

Figure 15B:
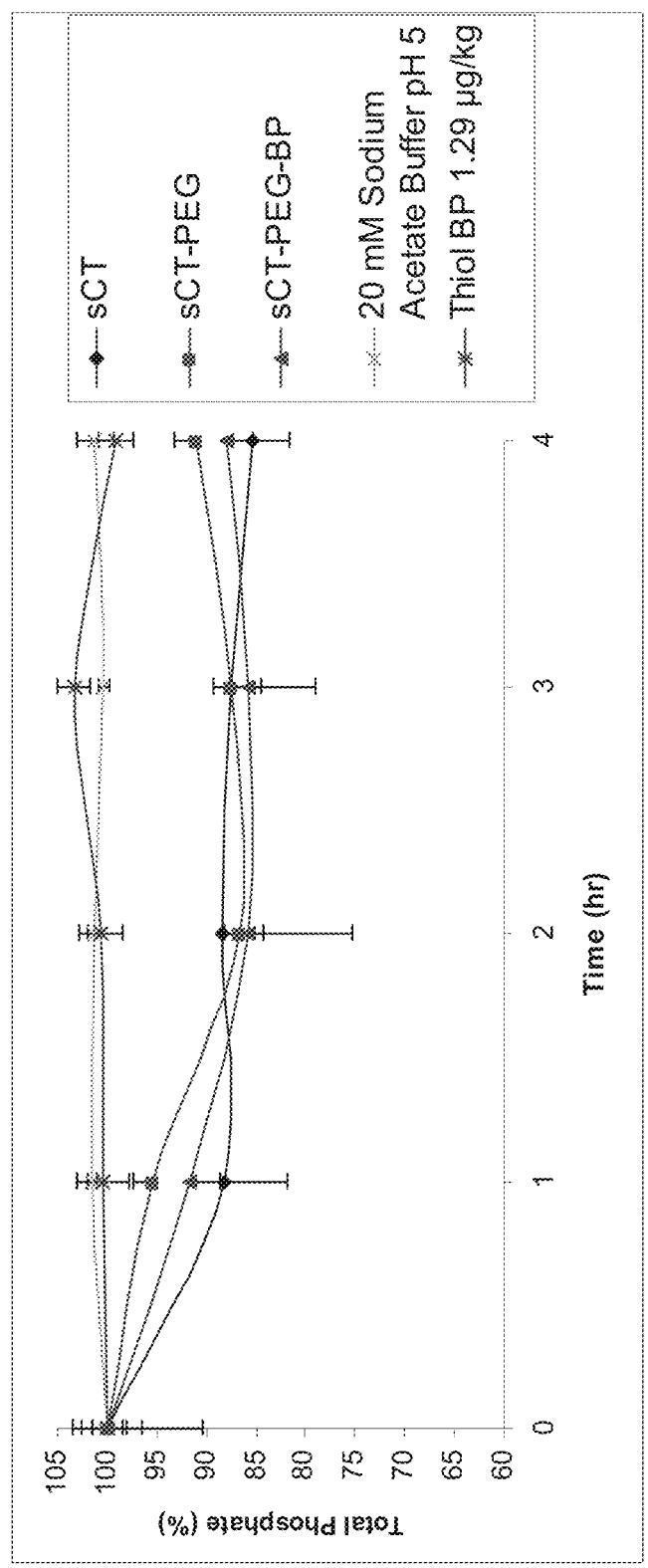

The effects of subcutaneously administered sCT, sCT-PEG and sCT-BP in terms of their effect on plasma phosphate level in normal rats (FIG. 15b) was also evaluated. At the beginning sCT had highest impact on phosphate level reduction. Total percentage of phosphate reduction induced by sCT, sCT-PEG and sCT-PEG-BP were 22.1±6.24%, 5.4±1.9% and 9.4±3.03% respectively at first hour. In the second hour after administration, sCT reduced plasma phosphate by 22.7±13.01%, sCT-PEG by 16.4±1.6% and sCT-PEG-BP by 15.3±1.5%. However, at the end of the experiment by 4 hour post dosing the total percentage phosphate level started to increase and the final decrease induced by sCT, sCT-PEG and sCT-PEG-BP were 15.7±3.7%, 9.06±2.1% and 12.00±2.56% respectively. All values were compared to the 20 mM Acetate buffer pH 5 treated controls over the same period. Similarly, the phosphate lowering effect of sCT-PEG-BP was confirmed to be due to sCT by dosing equivalent amount of thiol-BP alone in the same buffer.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed:

1. A composition comprising a peptide sequence and at least one bone targeting moiety, wherein the bone targeting moiety is bonded to the peptide sequence by a linker, wherein the peptide sequence comprises calcitonin, wherein the linker is a sulfosuccinimidyl-4-(N-maleimidomethyl)cyclohexane-1-carboxylate (sulfo-SMCC) and the bone targeting moiety is a residue of {2-[(3-mercaptopropyl)thio]ethane-1,1-diyl}bis(phosphonic acid), and wherein the composition is neutral or a pharmaceutically acceptable salt or ester thereof.

2. The composition of claim 1, wherein the peptide sequence comprises vertebrate calcitonin.

3. The composition of claim 2, wherein vertebrate calcitonin comprises salmon calcitonin, human calcitonin, pig calcitonin, eel calcitonin, ray fish salmon calcitonin, bovine calcitonin, chicken calcitonin, rat calcitonin, mouse calcitonin, bastard halibut or olive flounder calcitonin, dog calcitonin, sardine calcitonin, humpback salmon calcitonin, or any combination thereof.

4. The composition of claim 1, wherein the peptide sequence comprises a peptide sequence at least 90% identical to SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, and SEQ ID NO 15.

5. The composition of claim 1, wherein the linker is covalently bonded to a reactive amino group present in the peptide sequence.

6. The composition of claim 1, wherein the linker is covalently bonded to the N-terminus of the peptide sequence.

7. The composition of claim 1, wherein the peptide sequence comprises at least one lysine residue, and the linker is covalently bonded to the lysine residue by an amino group in lysine.

8. The composition of claim 1, wherein the peptide sequence comprises at least two lysine residues, and the linker is covalently bonded to the lysine residue by an amino group in lysine.

9. The composition of claim 1, wherein the peptide sequence comprises at least one lysine residue, and the linker is covalently bonded to the lysine residue by an amino group in lysine and the linker is bonded to the N-terminus of the peptide sequence.

10. The composition of claim 1, wherein the linker comprises a water soluble crosslinker.

11. The composition of claim 1, wherein the linker comprises a heterofunctional crosslinker, a homofunctional crosslinker, or a combination thereof.

12. The composition of claim 1, wherein the linker has at least one group capable of reacting with a nucleophile.

13. The composition of claim 1, wherein the peptide sequence is a salmon calcitonin peptide.

14. A pharmaceutical composition comprising the composition of claim 1 and a pharmaceutically acceptable carrier.

15. A method of making a composition comprising:
(a) reacting at least one amine group present in a peptide sequence with at least one linker, wherein the linker is a sulfosuccinimidyl-4-(N-maleimidomethyl)cyclohexane-1-carboxylate (sulfo-SMCC), to form a peptide linker intermediate, and
(b) reacting the peptide linker intermediate with a bisphosphonate containing compound, wherein the bisphosphonate containing compound is {2-[(3-mercaptopropyl)thio]ethane-1,1-diyl}bis(phosphonic acid).

16. The method of claim 15, wherein the peptide sequence comprises salmon calcitonin, human calcitonin, pig calcitonin, eel calcitonin, ray fish salmon calcitonin, bovine calcitonin, chicken calcitonin, rat calcitonin, mouse calcitonin, bastard halibut or olive flounder calcitonin, dog calcitonin, sardine calcitonin, humpback salmon calcitonin, or any combination thereof.

17. The method of claim 15, wherein the peptide sequence comprises a sequence at least 90% identical to SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, and SEQ ID NO 15.

18. The method of claim 15, wherein the ratio of the peptide sequence to linker comprises a 1:3, a 1:5, a 1:7, or a 1:10 mol/mol ratio.

19. The method of claim 15, wherein the reaction of step (a) comprises from 10 to 60 minutes at room temperature.

20. The method of claim 15, wherein the bisphosphonate containing compound comprises a thiol bisphosphonate compound.

21. The method of claim 15, wherein the ratio of the peptide linker intermediate to the bisphosphonate containing compound comprises a 1:3, a 1:5, a 1:7, a 1:10, or a 1:20 mol/mol ratio.

22. The method of claim 15, wherein step (b) comprises reacting the peptide linker intermediate with the bisphosphonate containing compound from 2 hours to 24 hours at room temperature.

23. A method of treating loss of bone mass in a subject comprising administering the composition of claim 1 to the subject having a condition that causes loss of bone mass.

24. A method for preventing a loss of bone in a subject comprising administering to the subject the composition of claim 1.

25. The method of claim 23, wherein the subject comprises a mammal.

26. The method of claim 23, wherein the subject comprises a human.

27. The method of claims 23, wherein the condition comprises osteoporosis, Paget's disease, osteolytic tumors, Rheumatoid Arthritis, Psoriatic Arthritis, Ankylosing Spondylitis, Osteoarthritis, hypercalcemia, osteopenia, or any combination thereof.

28. A method for reducing bone loss comprising contacting the bone with the composition of claim 1.

29. A method for preventing bone fractures comprising contacting the bone with the composition of claim 1.

* * * * *